US010449246B2

(12) United States Patent
Tian et al.

(10) Patent No.: US 10,449,246 B2
(45) Date of Patent: Oct. 22, 2019

(54) SUBUNIT VACCINE OF PORCINE PSEUDORABIES VIRUS AND PREPARATION METHOD

(71) Applicant: Pulike Biological Engineering, Inc., Henan (CN)

(72) Inventors: Kegong Tian, Henan (CN); Tongyan Wang, Henan (CN); Jinzhong Sun, Henan (CN); Xuke Zhang, Henan (CN)

(73) Assignee: Pulike Biological Engineering, Inc., Henan (CN)

( * ) Notice: Subject to any disclaimer, the term of this patent is extended or adjusted under 35 U.S.C. 154(b) by 64 days.

(21) Appl. No.: 15/738,462

(22) PCT Filed: Nov. 12, 2015

(86) PCT No.: PCT/CN2015/094478
§ 371 (c)(1),
(2) Date: Dec. 20, 2017

(87) PCT Pub. No.: WO2017/000470
PCT Pub. Date: Jan. 5, 2017

(65) Prior Publication Data

US 2018/0256705 A1 Sep. 13, 2018

(30) Foreign Application Priority Data

Jun. 29, 2015 (CN) .......................... 2015 1 0375665

(51) Int. Cl.
*A61K 39/245* (2006.01)
*A61P 31/22* (2006.01)
(Continued)

(52) U.S. Cl.
CPC ............ *A61K 39/245* (2013.01); *A61K 39/12* (2013.01); *A61K 39/39* (2013.01); *A61P 31/22* (2018.01);
(Continued)

(58) Field of Classification Search
None
See application file for complete search history.

(56) References Cited

U.S. PATENT DOCUMENTS

| | | | | |
|---|---|---|---|---|
| 5,196,516 A * | 3/1993 | Schreurs | .............. | C07K 14/005 424/229.1 |
| 6,207,165 B1 * | 3/2001 | Audonnet | ............ | A61K 39/102 424/199.1 |
| 2018/0256705 A1 * | 9/2018 | Tian | ..................... | A61K 39/245 |

FOREIGN PATENT DOCUMENTS

| | | |
|---|---|---|
| CN | 104004774 | 8/2014 |
| CN | 104248757 | 12/2014 |

OTHER PUBLICATIONS

Sequence alignment of SEQ ID No. 2 with UniProt database acc No. T2FL65_9ALPH Nov. 2013.*

(Continued)

*Primary Examiner* — Shanon A. Foley
(74) *Attorney, Agent, or Firm* — RatnerPrestia

(57) ABSTRACT

The present disclosure provides a PRV gB protein fragment, or a conservative variant or active fragment thereof, the gB protein fragment has a high level of expression, the subunit vaccine antigen prepared from the gB protein fragment has a better immune effect than a subunit vaccine antigen prepared from gB protein. The invention also provides a preparation method of a subunit vaccine by using the gB protein fragment alone, or the gB protein fragment together with gD protein. This vaccine has a simple preparation method and provides excellent protection against disease caused by the porcine pseudorabies virus.

13 Claims, 2 Drawing Sheets

Specification includes a Sequence Listing.

Note: Majority: SEQ ID NO:31; HN1201 gB.pro: SEQ ID NO:2; Bartha gB.pro:SEQ ID NO:28; Becker gB.pro: SEQ ID NO:29; Kaplan JF gB.pro: SEQ ID NO: 30.

(51) Int. Cl.
*A61K 39/39* (2006.01)
*A61K 39/12* (2006.01)
*C07K 14/005* (2006.01)
*A61K 39/00* (2006.01)

(52) U.S. Cl.
CPC ...... *C07K 14/005* (2013.01); *A61K 2039/525* (2013.01); *A61K 2039/552* (2013.01); *A61K 2039/70* (2013.01); *C07K 2319/00* (2013.01); *C12N 2710/16722* (2013.01); *C12N 2710/16734* (2013.01)

(56) References Cited

OTHER PUBLICATIONS

Sequence alignment of SEQ ID No. 4 with UniProt database acc No. T2FL65_9ALPH Nov. 2013.*
Sequence alignment of SEQ ID No. 6 with UniProt database acc No. G3G8Q6_9ALPH Nov. 2011.*
Sequence alignment of SEQ ID No. 8 with UniProt database acc No. G3G8X1_9ALPH Nov. 2011.*
Sequence alignment of SEQ ID No. 10 with Geneseq database acc No. AAP50035 Oct. 2003.*
Sequence alignment of SEQ ID No. 12 with PIR_80 database acc No. VGBE50 Mar. 1988.*
Nakamura et al. (Veterinary Microbiology. 1993; 36: 83-90).*
Marchioli et al. (Journal of Virology. 1987; 61 (12): 3977-3982).*
English Translation of Written Opinion issued by the International Searching Authority in International Application No. PCT/CN2015/094478, dated Mar. 16, 2016.
International Search Report in International Application No. PCT/CN2015/094478, dated Mar. 16, 2016.
Szpara, M.L., et al., "GenBank Accession No. AEM63980, Version AEM63980.1", GenBank, Nov. 2, 2011 (1 page).
English translation of Official Action issued in Japanese Application No. 2016-545343 filed Sep. 15, 2017 (4 pages).
Grimm, K.S., et al., "GenBank Accession No. AFI70792, Version AFI70792.1", GenBank, May 5, 2012 (1 page).
Yang, C.H., et al., GenBank Accession No. AAO46916, Version AAO46916.1, GenBank, Mar. 3, 2003 (1 page).
Szpara, M.L., et al., "GenBank Accession No. AEM64118, Version AEM64118.1", GenBank, Nov. 2, 2011 (1 page).

* cited by examiner

Note: Majority: SEQ ID NO:31; HN1201 gB.pro: SEQ ID NO:2; Bartha gB.pro:SEQ ID NO:28; Becker gB.pro: SEQ ID NO:29; Kaplan JF gB.pro: SEQ ID NO: 30.

Note: Majority: SEQ ID NO:31; HN1201 gB.pro: SEQ ID NO:2; Bartha gB.pro:SEQ ID NO:28; Becker gB.pro: SEQ ID NO:29; Kaplan JF gB.pro: SEQ ID NO: 30.

SEQUENCE LISTING

```
<160> NUMBER OF SEQ ID NOS: 27

<210> SEQ ID NO 1
<211> LENGTH: 2745
<212> TYPE: DNA
<213> ORGANISM: Pseudorabies virus

<400> SEQUENCE: 1

ctagggggcg tcggggtcct cgttctcgag gcgctggtag tgccggcggc gcgtggccat      60

cgccccgacg cggctggcca gcagcgcggg cccgctgttc ttcttgcgcg ccttgtgctc     120

ctgctgctcg agggccgaca cgatggacat gtaccggatc atgtcccggg cctggtccag     180

cttggcctcg tccacgtcgt cctcttcgac gccgtcctcc ttgagcgcct tcgtcgtgac     240

ggggtacagg gccttcatgg ggttgcggcg caggcgcgag atgtgccggt aggccaggaa     300

ggccgcgacc aggccggcca gcaccagcag cccgatggcg agcgccccga aggggttgga     360

caggaaggac accatgccgc cgacggccga gatcacggcc cccgtggcgc ccaggaccac     420

cttgccgacg gcggcgccca cgtcgccgag gccctggaag aagttggcga tgccgcgcag     480

cagcaccacg ttgtggtcca ccttgaccac gcggtcaatg tcgtagaact tgagcgcgtg     540

cagctggttg cggcgctgga tctcgctgta gtccaggagg cccgtgtcgg cgagctcctc     600

gcgcgtgtac acctcgaggg gcaggaactc gcggtcctcg agcagcgtca ggttcagggt     660

cacccgcgtg ctgatcgtct cgggcacctc caccatgcgc acgtagctgt agtcctcgta     720

gtacacgtac ccgccgccca gcttaaagta gcgccggtgg ttgccggtgc agggctcgat     780
```

-continued

```
gaggtcgcgc gagatgagga gctcgttgtc gtcgccgagc tggccctcga tcacgcccgt    840
gccgttgtgc tcgaaggtca ccagcgggcg gctgtagcac gtgccgcgct cgccgggcac    900
gcgcatggag ttctgcacgt acacgccgcc gcgcacctcc acgcaccgcg agatggccat    960
cacgtcgccg agcatgcgcg ccgagacgcg ctggcccagc gcggccgtgg ccacggcgct   1020
ggggttcagg cgcgacatct cgccccacag ggtgcggtcc ttgttctgca gctcgcacca   1080
ggcggccgcg atgcggctca gcatgtcgtt cacgtgcgcc tggatgtggt cgtaggtgaa   1140
ctgcaggcgc gcaaactcgg ccgagcccgt ggtgatgcgc aggtgccccg tgccgttgac   1200
ggccggcggc tcgggcgtcc ccgccgggcc gggggagcgc cgggcccgac gggcggccgc   1260
gggggacgcg gggcccacga cgccggcgag gccgaggcgc tcgagctcgc gcgcgtacag   1320
ctgcgccagc tcgttcgaga tcagcgggcg gaaggccacc acgaagcccc cgcgggcgag   1380
gtacacctcg ggcttgtcgc cggccagcac gtgcgtgttg ttgtagcgcc gccggtagat   1440
ggcgtcgatg gcctccgagg cctcgcggag gacgcagtcg cccaggtgca cgcgctgcag   1500
gtcgagctgc gtgacgtcgc tgacgaagga ggcgcccagg gcccgcgacg tgaagcggaa   1560
ggacccgtcg cgcgtctcgt cgcggatcat ctcctcggcc tcgcgccact tggccaggct   1620
gcacacgcgc cgcgtcttgg gggcccagtc ccaggccacc gtgaagtgcg gcgtgcgcag   1680
aaagttgcgc gtcacgctct cggaggcgcg gaggcgcgag tccaggtcga tggggtagta   1740
gtgctccacc tgctggaagc gcccgggcgc gtagccgatg tgctccccgt gggcccccctc  1800
gcgcaggccg tagaaggggg acatgtacac gatgtccccc gtggacaggg cgaaggagtc   1860
gtaggggtac acggagcgcg cctccacctc ctcgacgatg cagttgacgg aggtgcccgt   1920
gtggtagaag cccgcggcgc cgatcttggt gtaggtgtcg ttggtggtgt gccagccgcg   1980
ggtgccgagc gcgttcaggc gcgaggggcg caggtccacc tcgacggggt tctcgtcgcg   2040
gtcgaaggcg gtcaccttgt ggttgttgcg cacgtactcg gccttggaga cgcacttgcc   2100
gcggcggtcg atcacgtccg tgatctcctg cacggggacg ggcacgcggt ccgtgaagcg   2160
gttcgtgatg gccgcgtacg tgctcccgga ccacacggtc gtgacgatga cgttcttgta   2220
gtagatgtgg gccttgaact tgtgcggggc gatgttctcc ttgaagagca cggcgatccc   2280
ctccgtgaag ttgcgcccct gcgagtactc ggggcaggcc tgctcgggct ccaggcgcac   2340
caccgtggag ccggacggcg gcgggcagac gtagaagcgg tcccgctcgg tcgcggccgc   2400
gcgcacggcc gtgcgcgcgt ccaggtcgcc gtactcgccg tcgggggcgt ccgaggggcc   2460
gggggagacg gccccgtcga tctcctcgag ggactcctcc gcggagaagc cgtctggggt   2520
ggcgcccgtc ccgggcgcgg gcgaggccga ggcggcccgc gtcacggccg ccgcgccgca   2580
cgtcggggtc gcggcgagcg ccagcagcag cagcgctagc gcgacggcgc cccgcgcagc   2640
tgcagcgtgg tgtggagcag gccaaagacg tccgaggcca gcaccgccgt ggtgcccggg   2700
ccgatgcccg cggggcccgc gccaaagacc gccaccagcg ggcat                   2745
```

<210> SEQ ID NO 2
<211> LENGTH: 914
<212> TYPE: PRT
<213> ORGANISM: Pseudorabies virus

<400> SEQUENCE: 2

```
Met Pro Ala Gly Gly Gly Leu Trp Arg Gly Pro Arg Gly His Arg Pro
1               5                   10                  15

Gly His His Gly Gly Ala Gly Leu Gly Arg Leu Trp Pro Ala Pro His
```

-continued 20 25 30

His Ala Ala Ala Ala Arg Gly Ala Val Ala Leu Ala Leu Leu Leu Leu
35 40 45

Ala Leu Ala Ala Thr Pro Thr Cys Gly Ala Ala Ala Val Thr Arg Ala
50 55 60

Ala Ser Ala Ser Pro Ala Pro Gly Thr Gly Ala Thr Pro Asp Gly Phe
65 70 75 80

Ser Ala Glu Glu Ser Leu Glu Glu Ile Asp Gly Ala Val Ser Pro Gly
85 90 95

Pro Ser Asp Ala Pro Asp Gly Glu Tyr Gly Asp Leu Asp Ala Arg Thr
100 105 110

Ala Val Arg Ala Ala Ala Thr Glu Arg Asp Arg Phe Tyr Val Cys Pro
115 120 125

Pro Pro Ser Gly Ser Thr Val Val Arg Leu Glu Pro Glu Gln Ala Cys
130 135 140

Pro Glu Tyr Ser Gln Gly Arg Asn Phe Thr Glu Gly Ile Ala Val Leu
145 150 155 160

Phe Lys Glu Asn Ile Ala Pro His Lys Phe Lys Ala His Ile Tyr Tyr
165 170 175

Lys Asn Val Ile Val Thr Thr Val Trp Ser Gly Ser Thr Tyr Ala Ala
180 185 190

Ile Thr Asn Arg Phe Thr Asp Arg Val Pro Val Pro Val Gln Glu Ile
195 200 205

Thr Asp Val Ile Asp Arg Arg Gly Lys Cys Val Ser Lys Ala Glu Tyr
210 215 220

Val Arg Asn Asn His Lys Val Thr Ala Phe Asp Arg Asp Glu Asn Pro
225 230 235 240

Val Glu Val Asp Leu Arg Pro Ser Arg Leu Asn Ala Leu Gly Thr Arg
245 250 255

Gly Trp His Thr Thr Asn Asp Thr Tyr Thr Lys Ile Gly Ala Ala Gly
260 265 270

Phe Tyr His Thr Gly Thr Ser Val Asn Cys Ile Val Glu Glu Val Glu
275 280 285

Ala Arg Ser Val Tyr Pro Tyr Asp Ser Phe Ala Leu Ser Thr Gly Asp
290 295 300

Ile Val Tyr Met Ser Pro Phe Tyr Gly Leu Arg Glu Gly Ala His Gly
305 310 315 320

Glu His Ile Gly Tyr Ala Pro Gly Arg Phe Gln Gln Val Glu His Tyr
325 330 335

Tyr Pro Ile Asp Leu Asp Ser Arg Leu Arg Ala Ser Glu Ser Val Thr
340 345 350

Arg Asn Phe Leu Arg Thr Pro His Phe Thr Val Ala Trp Asp Trp Ala
355 360 365

Pro Lys Thr Arg Arg Val Cys Ser Leu Ala Lys Trp Arg Glu Ala Glu
370 375 380

Glu Met Ile Arg Asp Glu Thr Arg Asp Gly Ser Phe Arg Phe Thr Ser
385 390 395 400

Arg Ala Leu Gly Ala Ser Phe Val Ser Asp Val Thr Gln Leu Asp Leu
405 410 415

Gln Arg Val His Leu Gly Asp Cys Val Leu Arg Glu Ala Ser Glu Ala
420 425 430

Ile Asp Ala Ile Tyr Arg Arg Arg Tyr Asn Asn Thr His Val Leu Ala
435 440 445

-continued

```
Gly Asp Lys Pro Glu Val Tyr Leu Ala Arg Gly Gly Phe Val Val Ala
    450                 455                 460

Phe Arg Pro Leu Ile Ser Asn Glu Leu Ala Gln Leu Tyr Ala Arg Glu
465                 470                 475                 480

Leu Glu Arg Leu Gly Leu Ala Gly Val Val Gly Pro Ala Ser Pro Ala
                485                 490                 495

Ala Ala Arg Arg Ala Arg Arg Ser Pro Gly Pro Ala Gly Thr Pro Glu
            500                 505                 510

Pro Pro Ala Val Asn Gly Thr Gly His Leu Arg Ile Thr Thr Gly Ser
        515                 520                 525

Ala Glu Phe Ala Arg Leu Gln Phe Thr Tyr Asp His Ile Gln Ala His
    530                 535                 540

Val Asn Asp Met Leu Ser Arg Ile Ala Ala Ala Trp Cys Glu Leu Gln
545                 550                 555                 560

Asn Lys Asp Arg Thr Leu Trp Gly Glu Met Ser Arg Leu Asn Pro Ser
                565                 570                 575

Ala Val Ala Thr Ala Ala Leu Gly Gln Arg Val Ser Ala Arg Met Leu
            580                 585                 590

Gly Asp Val Met Ala Ile Ser Arg Cys Val Glu Val Arg Gly Gly Val
        595                 600                 605

Tyr Val Gln Asn Ser Met Arg Val Pro Gly Glu Arg Gly Thr Cys Tyr
    610                 615                 620

Ser Arg Pro Leu Val Thr Phe Glu His Asn Gly Thr Gly Val Ile Glu
625                 630                 635                 640

Gly Gln Leu Gly Asp Asp Asn Glu Leu Leu Ile Ser Arg Asp Leu Ile
                645                 650                 655

Glu Pro Cys Thr Gly Asn His Arg Arg Tyr Phe Lys Leu Gly Gly Gly
            660                 665                 670

Tyr Val Tyr Tyr Glu Asp Tyr Ser Tyr Val Arg Met Val Glu Val Pro
        675                 680                 685

Glu Thr Ile Ser Thr Arg Val Thr Leu Asn Leu Thr Leu Leu Glu Asp
    690                 695                 700

Arg Glu Phe Leu Pro Leu Glu Val Tyr Thr Arg Glu Glu Leu Ala Asp
705                 710                 715                 720

Thr Gly Leu Leu Asp Tyr Ser Glu Ile Gln Arg Arg Asn Gln Leu His
                725                 730                 735

Ala Leu Lys Phe Tyr Asp Ile Asp Arg Val Val Lys Val Asp His Asn
            740                 745                 750

Val Val Leu Leu Arg Gly Ile Ala Asn Phe Phe Gln Gly Leu Gly Asp
        755                 760                 765

Val Gly Ala Ala Val Gly Lys Val Val Leu Gly Ala Thr Gly Ala Val
    770                 775                 780

Ile Ser Ala Val Gly Gly Met Val Ser Phe Leu Ser Asn Pro Phe Gly
785                 790                 795                 800

Ala Leu Ala Ile Gly Leu Leu Val Leu Ala Gly Leu Val Ala Ala Phe
                805                 810                 815

Leu Ala Tyr Arg His Ile Ser Arg Leu Arg Arg Asn Pro Met Lys Ala
            820                 825                 830

Leu Tyr Pro Val Thr Thr Lys Ala Leu Lys Glu Asp Gly Val Glu Glu
        835                 840                 845

Asp Asp Val Asp Glu Ala Lys Leu Asp Gln Ala Arg Asp Met Ile Arg
    850                 855                 860
```

-continued

```
Tyr Met Ser Ile Val Ser Ala Leu Glu Gln Gln Glu His Lys Ala Arg
865                 870                 875                 880

Lys Lys Asn Ser Gly Pro Ala Leu Leu Ala Ser Arg Val Gly Ala Met
                885                 890                 895

Ala Thr Arg Arg Arg His Tyr Gln Arg Leu Glu Asn Glu Asp Pro Asp
            900                 905                 910

Ala Pro


<210> SEQ ID NO 3
<211> LENGTH: 738
<212> TYPE: DNA
<213> ORGANISM: Pseudorabies virus

<400> SEQUENCE: 3

acgcgggccg cctcggcctc gcccgcgccc gggacgggcg ccaccccaga cggcttctcc      60

gcggaggagt ccctcgagga gatcgacggg gccgtctccc ccggcccctc ggacgccccc     120

gacggcgagt acggcgacct ggacgcgcgc acggccgtgc gcgcggccgc gaccgagcgg     180

gaccgcttct acgtctgccc gccgccgtcc ggctccacgg tggtgcgcct ggagcccgag     240

caggcctgcc ccgagtactc gggtggttct ggtaacgaca tgctgagccg catcgcggcc     300

gcctggtgcg agctgcagaa caaggaccgc accctgtggg gcgagatgtc gcgcctgaac     360

cccagcgccg tggccacggc cgcgctgggc cagcgcgtct cggcgcgcat gctcggcgac     420

gtgatggcca tctcgcggtg cgtggaggtg cgcggcggcg tgtacgtgca gaactccatg     480

cgcgtgcccg gcgagcgcgg cacgtgctac agccgcccgc tggtgacctt cgagcacaac     540

ggcacgggcg tgatcgaggg ccagctcggc gacgacaacg agctcctcat ctcgcgcgac     600

ctcatcgagc cctgcaccgg caaccaccgg cgctacttta agctgggcgg cgggtacgtg     660

tactacgagg actacagcta cgtgcgcatg gtggaggtgc ccgagacgat cagcacgcgg     720

gtgaccctga acctgacg                                                   738


<210> SEQ ID NO 4
<211> LENGTH: 246
<212> TYPE: PRT
<213> ORGANISM: Pseudorabies virus

<400> SEQUENCE: 4

Thr Arg Ala Ala Ser Ala Ser Pro Ala Pro Gly Thr Gly Ala Thr Pro
1               5                   10                  15

Asp Gly Phe Ser Ala Glu Glu Ser Leu Glu Glu Ile Asp Gly Ala Val
            20                  25                  30

Ser Pro Gly Pro Ser Asp Ala Pro Asp Gly Glu Tyr Gly Asp Leu Asp
        35                  40                  45

Ala Arg Thr Ala Val Arg Ala Ala Ala Thr Glu Arg Asp Arg Phe Tyr
    50                  55                  60

Val Cys Pro Pro Pro Ser Gly Ser Thr Val Val Arg Leu Glu Pro Glu
65                  70                  75                  80

Gln Ala Cys Pro Glu Tyr Ser Gly Gly Ser Gly Asn Asp Met Leu Ser
                85                  90                  95

Arg Ile Ala Ala Ala Trp Cys Glu Leu Gln Asn Lys Asp Arg Thr Leu
            100                 105                 110

Trp Gly Glu Met Ser Arg Leu Asn Pro Ser Ala Val Ala Thr Ala Ala
        115                 120                 125

Leu Gly Gln Arg Val Ser Ala Arg Met Leu Gly Asp Val Met Ala Ile
    130                 135                 140
```

```
Ser Arg Cys Val Glu Val Arg Gly Gly Val Tyr Val Gln Asn Ser Met
145                 150                 155                 160

Arg Val Pro Gly Glu Arg Gly Thr Cys Tyr Ser Arg Pro Leu Val Thr
                165                 170                 175

Phe Glu His Asn Gly Thr Gly Val Ile Glu Gly Gln Leu Gly Asp Asp
            180                 185                 190

Asn Glu Leu Leu Ile Ser Arg Asp Leu Ile Glu Pro Cys Thr Gly Asn
        195                 200                 205

His Arg Arg Tyr Phe Lys Leu Gly Gly Gly Tyr Val Tyr Tyr Glu Asp
    210                 215                 220

Tyr Ser Tyr Val Arg Met Val Glu Val Pro Glu Thr Ile Ser Thr Arg
225                 230                 235                 240

Val Thr Leu Asn Leu Thr
                245


<210> SEQ ID NO 5
<211> LENGTH: 744
<212> TYPE: DNA
<213> ORGANISM: Pseudorabies virus

<400> SEQUENCE: 5

acgcgggccg cctcggcctc gccgacgccc gtcccgggca gccccggcct cacccccaac      60

gacgtctccg cggaggcgtc cctcgaggag atcgaggcgt tcacccccgg cccctcggag     120

gcccccgacg gcgagtacgg cgacctggac gcgcgcacgg ccgtgcgcgc ggccgcgacc     180

gagcgggacc gcttctacgt ctgcccgccg ccgtccggct ccacggtggt gcgcctggag     240

cccgagcagg cctgccccga gtactcgggt ggttctggta acgacatgct gggccgcatc     300

gcggccgcct ggtgcgagct gcagaacaag gaccgcaccc tgtggagcga gatgtcgcgc     360

ctgaacccca gcgccgtggc cacggccgcg ctcggccagc gcgtctcggc gcgcatgctc     420

ggcgacgtga tggccatctc gcggtgcgtg gaggtgcgcg gcggcgtgta cgtgcagaac     480

tccatgcgcg tgcccggcga gcgcggcacg tgctacagcc gcccgctggt caccttcgag     540

cacaacggca cgggcgtgat cgagggccag ctcggcgacg acaacgagct cctcatctcg     600

cgcgacctca tcgagccctg caccggcaac caccggcgct actttaagct ggggagcggg     660

tacgtgtact acgaggacta cagctacgtg cgcatggtgg aggtgcccga gacgatcagc     720

acgcgggtga ccctgaacct gacg                                            744


<210> SEQ ID NO 6
<211> LENGTH: 248
<212> TYPE: PRT
<213> ORGANISM: Pseudorabies virus

<400> SEQUENCE: 6

Thr Arg Ala Ala Ser Ala Ser Pro Thr Pro Val Pro Gly Ser Pro Gly
1               5                   10                  15

Leu Thr Pro Asn Asp Val Ser Ala Glu Ala Ser Leu Glu Glu Ile Glu
            20                  25                  30

Ala Phe Thr Pro Gly Pro Ser Glu Ala Pro Asp Gly Glu Tyr Gly Asp
        35                  40                  45

Leu Asp Ala Arg Thr Ala Val Arg Ala Ala Ala Thr Glu Arg Asp Arg
    50                  55                  60

Phe Tyr Val Cys Pro Pro Pro Ser Gly Ser Thr Val Val Arg Leu Glu
65                  70                  75                  80
```

-continued

Pro Glu Gln Ala Cys Pro Glu Tyr Ser Gly Gly Ser Gly Asn Asp Met
                85                  90                  95

Leu Gly Arg Ile Ala Ala Ala Trp Cys Glu Leu Gln Asn Lys Asp Arg
            100                 105                 110

Thr Leu Trp Ser Glu Met Ser Arg Leu Asn Pro Ser Ala Val Ala Thr
        115                 120                 125

Ala Ala Leu Gly Gln Arg Val Ser Ala Arg Met Leu Gly Asp Val Met
    130                 135                 140

Ala Ile Ser Arg Cys Val Glu Val Arg Gly Gly Val Tyr Val Gln Asn
145                 150                 155                 160

Ser Met Arg Val Pro Gly Glu Arg Gly Thr Cys Tyr Ser Arg Pro Leu
                165                 170                 175

Val Thr Phe Glu His Asn Gly Thr Gly Val Ile Glu Gly Gln Leu Gly
            180                 185                 190

Asp Asp Asn Glu Leu Leu Ile Ser Arg Asp Leu Ile Glu Pro Cys Thr
        195                 200                 205

Gly Asn His Arg Arg Tyr Phe Lys Leu Gly Ser Gly Tyr Val Tyr Tyr
    210                 215                 220

Glu Asp Tyr Ser Tyr Val Arg Met Val Glu Val Pro Glu Thr Ile Ser
225                 230                 235                 240

Thr Arg Val Thr Leu Asn Leu Thr
                245

<210> SEQ ID NO 7
<211> LENGTH: 756
<212> TYPE: DNA
<213> ORGANISM: Pseudorabies virus

<400> SEQUENCE: 7
acgcgggccg cctcggcctc gccgacgccc gtcccgggca gccccggcct cacccccaac 60
gacgtctccg cggaggcgtc cctcgaggag atcgaggcgt tcacccccgg cccctcggag 120
gcccccgacg gcgagtacgg cgacctggac gcgcgcacgg ccgtgcgcgc ggccgtgcgc 180
gcggccgcga ccgagcggga ccgcttctac gtctgcccgc cgccgtccgg ctccacggtg 240
gtgcgcctgg agcccgagca ggcctgcccc gagtactcgg gtggttctgg taacgacatg 300
ctgggccgca tcgcgaccgc ctggtgcgag ctgcagaaca aggaccgcac cctgtggagc 360
gagatgtcgc gcctgaaccc cagcgccgtg gccacggccg cgctcggcca gcgcgtctcg 420
gcgcgcatgc tcggcgacgt gatggccatc tcgcggtgcg tggaggtgcg cggcggcgtg 480
tacgtgcaga actccatgcg cgtgcccggc gagcgcggca cgtgctacag ccgcccgctg 540
gtcaccttcg agcacaacgg cacgggcgtg atcgagggcc agctcggcga cgacaacgag 600
ctcctcatct cgcgcgacct catcgagccc tgcaccggca accaccggcg ctactttaag 660
ctggggagcg ggtacgtgta ctacgaggac tacagctacg tgcgcatggt ggaggtgccc 720
gagacgatca gcacgcgggt gaccctgaac ctgacg 756

<210> SEQ ID NO 8
<211> LENGTH: 252
<212> TYPE: PRT
<213> ORGANISM: Pseudorabies virus

<400> SEQUENCE: 8

Thr Arg Ala Ala Ser Ala Ser Pro Thr Pro Val Pro Gly Ser Pro Gly
1               5                   10                  15

Leu Thr Pro Asn Asp Val Ser Ala Glu Ala Ser Leu Glu Glu Ile Glu

-continued

```
            20                  25                  30

Ala Phe Thr Pro Gly Pro Ser Glu Ala Pro Asp Gly Glu Tyr Gly Asp
        35                  40                  45

Leu Asp Ala Arg Thr Ala Val Arg Ala Ala Val Arg Ala Ala Ala Thr
    50                  55                  60

Glu Arg Asp Arg Phe Tyr Val Cys Pro Pro Pro Ser Gly Ser Thr Val
65                  70                  75                  80

Val Arg Leu Glu Pro Glu Gln Ala Cys Pro Glu Tyr Ser Gly Gly Ser
                85                  90                  95

Gly Asn Asp Met Leu Gly Arg Ile Ala Thr Ala Trp Cys Glu Leu Gln
            100                 105                 110

Asn Lys Asp Arg Thr Leu Trp Ser Glu Met Ser Arg Leu Asn Pro Ser
        115                 120                 125

Ala Val Ala Thr Ala Ala Leu Gly Gln Arg Val Ser Ala Arg Met Leu
    130                 135                 140

Gly Asp Val Met Ala Ile Ser Arg Cys Val Glu Val Arg Gly Gly Val
145                 150                 155                 160

Tyr Val Gln Asn Ser Met Arg Val Pro Gly Glu Arg Gly Thr Cys Tyr
                165                 170                 175

Ser Arg Pro Leu Val Thr Phe Glu His Asn Gly Thr Gly Val Ile Glu
            180                 185                 190

Gly Gln Leu Gly Asp Asp Asn Glu Leu Leu Ile Ser Arg Asp Leu Ile
        195                 200                 205

Glu Pro Cys Thr Gly Asn His Arg Arg Tyr Phe Lys Leu Gly Ser Gly
    210                 215                 220

Tyr Val Tyr Tyr Glu Asp Tyr Ser Tyr Val Arg Met Val Glu Val Pro
225                 230                 235                 240

Glu Thr Ile Ser Thr Arg Val Thr Leu Asn Leu Thr
                245                 250
```

<210> SEQ ID NO 9
<211> LENGTH: 735
<212> TYPE: DNA
<213> ORGANISM: Pseudorabies virus

<400> SEQUENCE: 9

```
acgcgggccg cctcggcctc gccgacgccc gggacgggcg ccacccccaa cgacgtctcc      60

gcggaggcgt ccctcgagga gatcgaggcg ttctcccccg gcccctcgga ggcccccgac     120

ggcgagtacg gcgacctgga cgcgcggacg gccgtgcgcg cggccgcgac cgagcgggac     180

cgcttctacg tctgcccgcc gccgtccggc tccacggtgg tgcggctgga gcccgagcag     240

gcctgccccg agtactcggg tggttctggt aacgacatgc tgggccgcat cgcggccgcc     300

tggtgcgagc tgcagaacaa ggaccgcacc ctgtggagcg agatgtcgcg cctgaacccc     360

agcgccgtgg ccacggccgc gctcggccag cgcgtctcgg cgcgcatgct cggcgacgtg     420

atggccatct cgcggtgcgt ggaggtgcgc ggcggcgtgt acgtgcagaa ctccatgcgc     480

gtgcccggcg agcgcggcac gtgctacagc cgcccgctgg tcaccttcga gcacaacggc     540

acgggcgtga tcgagggcca gctcggcgac gacaacgagc tcctcatctc gcgcgacctc     600

atcgagccct gcaccggcaa ccaccggcgc tactttaagc tggggagcgg gtacgtgtac     660

tacgaggact acaactacgt gcgcatggtg gaggtgcccg agacgatcag cacgcgggtg     720

accctgaacc tgacg                                                      735
```

-continued

<210> SEQ ID NO 10
<211> LENGTH: 245
<212> TYPE: PRT
<213> ORGANISM: Pseudorabies virus

<400> SEQUENCE: 10

```
Thr Arg Ala Ala Ser Ala Ser Pro Thr Pro Gly Thr Gly Ala Thr Pro
1               5                   10                  15

Asn Asp Val Ser Ala Glu Ala Ser Leu Glu Glu Ile Glu Ala Phe Ser
            20                  25                  30

Pro Gly Pro Ser Glu Ala Pro Asp Gly Glu Tyr Gly Asp Leu Asp Ala
        35                  40                  45

Arg Thr Ala Val Arg Ala Ala Ala Thr Glu Arg Asp Arg Phe Tyr Val
    50                  55                  60

Cys Pro Pro Pro Ser Gly Ser Thr Val Val Arg Leu Glu Pro Glu Gln
65                  70                  75                  80

Ala Cys Pro Glu Tyr Ser Gly Gly Ser Gly Asn Asp Met Leu Gly Arg
                85                  90                  95

Ile Ala Ala Ala Trp Cys Glu Leu Gln Asn Lys Asp Arg Thr Leu Trp
            100                 105                 110

Ser Glu Met Ser Arg Leu Asn Pro Ser Ala Val Ala Thr Ala Ala Leu
        115                 120                 125

Gly Gln Arg Val Ser Ala Arg Met Leu Gly Asp Val Met Ala Ile Ser
    130                 135                 140

Arg Cys Val Glu Val Arg Gly Gly Val Tyr Val Gln Asn Ser Met Arg
145                 150                 155                 160

Val Pro Gly Glu Arg Gly Thr Cys Tyr Ser Arg Pro Leu Val Thr Phe
                165                 170                 175

Glu His Asn Gly Thr Gly Val Ile Glu Gly Gln Leu Gly Asp Asp Asn
            180                 185                 190

Glu Leu Leu Ile Ser Arg Asp Leu Ile Glu Pro Cys Thr Gly Asn His
        195                 200                 205

Arg Arg Tyr Phe Lys Leu Gly Ser Gly Tyr Val Tyr Tyr Glu Asp Tyr
    210                 215                 220

Asn Tyr Val Arg Met Val Glu Val Pro Glu Thr Ile Ser Thr Arg Val
225                 230                 235                 240

Thr Leu Asn Leu Thr
                245
```

<210> SEQ ID NO 11
<211> LENGTH: 1008
<212> TYPE: DNA
<213> ORGANISM: Pseudorabies virus

<400> SEQUENCE: 11

```
gcggacgtgg acgccgtgcc cgcgccgacc ttccccccgc ccgcgtaccc gtacaccgag     60

tcgtggcagc tgacgctgac gacggtcccc tcgcccttcg tcggccccgc ggacgtctac    120

cacacgcgcc cgctggagga cccgtgcggg gtggtggcgc tgatctccga cccgcaggtg    180

gaccggctgc tgaacgaggc ggtggcccac cggcggccca cgtaccgcgc ccacgtggcc    240

tggtaccgca tcgcggacgg gtgcgcgcac ctgctgtact ttatcgagta cgccgactgc    300

gaccccaggc agatctttgg gcgctgccgg cgccgcacca cgccgatgtg gtggaccccg    360

tccgcggact acatgttccc cacggaggac gagctggggc tgctcatggt ggccccgggg    420

cggttcaacg agggccagta ccggcgcctg gtgtccgtcg acggcgtgaa catcctcacc    480
```

-continued

```
gacttcatgg tggcgctccc cgaggggcaa gagtgcccgt tcgcccgcgt ggaccagcac     540

cgcacgtaca agttcggcgc gtgctggagc gacgacagct tcaagcgggg cgtggacgtg     600

atgcgattcc tgacgccgtt ctaccagcag cccccgcacc gggaggtggt gaactactgg     660

taccgcaaga acggccggac gctcccgcgg gcctacgccg ccgccacgcc gtacgccatc     720

gaccccgcgc ggccctcggc gggctcgccg aggcccaggc cccggccccg gcccaggccc     780

cggccgaagc ccgagcccgc cccggcgacg cccgcgcccc ccggccgcct gcccgagccg     840

gcgacgcggg accacgccgc cggggggcgc cccacgccgc gacccccgag gcccgagacg     900

ccgcaccgcc ccttcgcccc gccggccgtc gtgcccagcg ggtggccgca gcccgcggag     960

ccgttcccgc cccggaccac cgccgcgccg ggcgtctcgc gccaccgc                 1008
```

<210> SEQ ID NO 12
<211> LENGTH: 336
<212> TYPE: PRT
<213> ORGANISM: Pseudorabies virus

<400> SEQUENCE: 12

```
Ala Asp Val Asp Ala Val Pro Ala Pro Thr Phe Pro Pro Pro Ala Tyr
1               5                   10                  15

Pro Tyr Thr Glu Ser Trp Gln Leu Thr Leu Thr Thr Val Pro Ser Pro
            20                  25                  30

Phe Val Gly Pro Ala Asp Val Tyr His Thr Arg Pro Leu Glu Asp Pro
        35                  40                  45

Cys Gly Val Val Ala Leu Ile Ser Asp Pro Gln Val Asp Arg Leu Leu
    50                  55                  60

Asn Glu Ala Val Ala His Arg Arg Pro Thr Tyr Arg Ala His Val Ala
65                  70                  75                  80

Trp Tyr Arg Ile Ala Asp Gly Cys Ala His Leu Leu Tyr Phe Ile Glu
                85                  90                  95

Tyr Ala Asp Cys Asp Pro Arg Gln Ile Phe Gly Arg Cys Arg Arg Arg
            100                 105                 110

Thr Thr Pro Met Trp Trp Thr Pro Ser Ala Asp Tyr Met Phe Pro Thr
        115                 120                 125

Glu Asp Glu Leu Gly Leu Leu Met Val Ala Pro Gly Arg Phe Asn Glu
    130                 135                 140

Gly Gln Tyr Arg Arg Leu Val Ser Val Asp Gly Val Asn Ile Leu Thr
145                 150                 155                 160

Asp Phe Met Val Ala Leu Pro Glu Gly Gln Glu Cys Pro Phe Ala Arg
                165                 170                 175

Val Asp Gln His Arg Thr Tyr Lys Phe Gly Ala Cys Trp Ser Asp Asp
            180                 185                 190

Ser Phe Lys Arg Gly Val Asp Val Met Arg Phe Leu Thr Pro Phe Tyr
        195                 200                 205

Gln Gln Pro Pro His Arg Glu Val Val Asn Tyr Trp Tyr Arg Lys Asn
    210                 215                 220

Gly Arg Thr Leu Pro Arg Ala Tyr Ala Ala Ala Thr Pro Tyr Ala Ile
225                 230                 235                 240

Asp Pro Ala Arg Pro Ser Ala Gly Ser Pro Arg Pro Arg Pro Arg Pro
                245                 250                 255

Arg Pro Arg Pro Arg Pro Lys Pro Glu Pro Ala Pro Ala Thr Pro Ala
            260                 265                 270

Pro Pro Gly Arg Leu Pro Glu Pro Ala Thr Arg Asp His Ala Ala Gly
        275                 280                 285
```

Gly Arg Pro Thr Pro Arg Pro Pro Arg Pro Glu Thr Pro His Arg Pro
    290                 295                 300

Phe Ala Pro Pro Ala Val Val Pro Ser Gly Trp Pro Gln Pro Ala Glu
305                 310                 315                 320

Pro Phe Pro Pro Arg Thr Thr Ala Ala Pro Gly Val Ser Arg His Arg
                325                 330                 335

<210> SEQ ID NO 13
<211> LENGTH: 1746
<212> TYPE: DNA
<213> ORGANISM: Pseudorabies virus

<400> SEQUENCE: 13
acgcgggccg cctcggcctc gcccgcgccc gggacgggcg ccaccccaga cggcttctcc 60
gcggaggagt ccctcgagga gatcgacggg gccgtctccc ccggcccctc ggacgccccc 120
gacggcgagt acggcgacct ggacgcgcgc acggccgtgc gcgcggccgc gaccgagcgg 180
gaccgcttct acgtctgccc gccgccgtcc ggctccacgg tggtgcgcct ggagcccgag 240
caggcctgcc ccgagtactc gggtggttct ggtaacgaca tgctgagccg catcgcggcc 300
gcctggtgcg agctgcagaa caaggaccgc accctgtggg gcgagatgtc gcgcctgaac 360
cccagcgccg tggccacggc cgcgctgggc cagcgcgtct cggcgcgcat gctcggcgac 420
gtgatggcca tctcgcggtg cgtggaggtg cgcggcggcg tgtacgtgca gaactccatg 480
cgcgtgcccg gcgagcgcgg cacgtgctac agccgcccgc tggtgacctt cgagcacaac 540
ggcacgggcg tgatcgaggg ccagctcggc gacgacaacg agctcctcat ctcgcgcgac 600
ctcatcgagc cctgcaccgg caaccaccgg cgctacttta agctgggcgg cgggtacgtg 660
tactacgagg actacagcta cgtgcgcatg gtggaggtgc ccgagacgat cagcacgcgg 720
gtgaccctga acctgacggc ggacgtggac gccgtgcccg cgccgacctt cccccgcccc 780
gcgtacccgt acaccgagtc gtggcagctg acgctgacga cggtcccctc gcccttcgtc 840 ggcccccgcgg acgtctacca cacgcgcccg ctggaggacc cgtgcggggt ggtggcgctg 900
atctccgacc cgcaggtgga ccggctgctg aacgaggcgg tggcccaccg gcggcccacg 960
taccgcgccc acgtggcctg gtaccgcatc gcggacgggt gcgcgcacct gctgtacttt 1020
atcgagtacg ccgactgcga ccccaggcag atctttgggc gctgccggcg ccgcaccacg 1080
ccgatgtggt ggaccccgtc cgcggactac atgttcccca cggaggacga gctggggctg 1140
ctcatggtgg ccccggggcg gttcaacgag ggccagtacc ggcgcctggt gtccgtcgac 1200
ggcgtgaaca tcctcaccga cttcatggtg gcgctccccg aggggcaaga gtgcccgttc 1260
gcccgcgtgg accagcaccg cacgtacaag ttcggcgcgt gctggagcga cgacagcttc 1320
aagcggggcg tggacgtgat gcgattcctg acgccgttct accagcagcc cccgcaccgg 1380
gaggtggtga actactggta ccgcaagaac ggccggacgc tcccgcgggc ctacgccgcc 1440
gccacgccgt acgccatcga ccccgcgcgg ccctcggcgg gctcgccgag gcccaggccc 1500
cggccccggc ccaggccccg gccgaagccc gagcccgccc cggcgacgcc cgcgcccccc 1560
ggccgcctgc ccgagccggc gacgcgggac cacgccgccg gggggcgccc cacgccgcga 1620
cccccgaggc ccgagacgcc gcaccgcccc ttcgccccgc cggccgtcgt gcccagcggg 1680
tggccgcagc ccgcggagcc gttcccgccc cggaccaccg ccgcgccggg cgtctcgcgc 1740
caccgc 1746

-continued

```
<210> SEQ ID NO 14
<211> LENGTH: 582
<212> TYPE: PRT
<213> ORGANISM: Pseudorabies virus

<400> SEQUENCE: 14

Thr Arg Ala Ala Ser Ala Ser Pro Ala Pro Gly Thr Gly Ala Thr Pro
1               5                   10                  15

Asp Gly Phe Ser Ala Glu Glu Ser Leu Glu Glu Ile Asp Gly Ala Val
            20                  25                  30

Ser Pro Gly Pro Ser Asp Ala Pro Asp Gly Glu Tyr Gly Asp Leu Asp
        35                  40                  45

Ala Arg Thr Ala Val Arg Ala Ala Ala Thr Glu Arg Asp Arg Phe Tyr
    50                  55                  60

Val Cys Pro Pro Pro Ser Gly Ser Thr Val Val Arg Leu Glu Pro Glu
65                  70                  75                  80

Gln Ala Cys Pro Glu Tyr Ser Gly Gly Ser Gly Asn Asp Met Leu Ser
                85                  90                  95

Arg Ile Ala Ala Ala Trp Cys Glu Leu Gln Asn Lys Asp Arg Thr Leu
            100                 105                 110

Trp Gly Glu Met Ser Arg Leu Asn Pro Ser Ala Val Ala Thr Ala Ala
        115                 120                 125

Leu Gly Gln Arg Val Ser Ala Arg Met Leu Gly Asp Val Met Ala Ile
    130                 135                 140

Ser Arg Cys Val Glu Val Arg Gly Gly Val Tyr Val Gln Asn Ser Met
145                 150                 155                 160

Arg Val Pro Gly Glu Arg Gly Thr Cys Tyr Ser Arg Pro Leu Val Thr
                165                 170                 175

Phe Glu His Asn Gly Thr Gly Val Ile Glu Gly Gln Leu Gly Asp Asp
            180                 185                 190

Asn Glu Leu Leu Ile Ser Arg Asp Leu Ile Glu Pro Cys Thr Gly Asn
        195                 200                 205

His Arg Arg Tyr Phe Lys Leu Gly Gly Gly Tyr Val Tyr Tyr Glu Asp
    210                 215                 220

Tyr Ser Tyr Val Arg Met Val Glu Val Pro Glu Thr Ile Ser Thr Arg
225                 230                 235                 240

Val Thr Leu Asn Leu Thr Ala Asp Val Asp Ala Val Pro Ala Pro Thr
                245                 250                 255

Phe Pro Pro Pro Ala Tyr Pro Tyr Thr Glu Ser Trp Gln Leu Thr Leu
            260                 265                 270

Thr Thr Val Pro Ser Pro Phe Val Gly Pro Ala Asp Val Tyr His Thr
        275                 280                 285

Arg Pro Leu Glu Asp Pro Cys Gly Val Val Ala Leu Ile Ser Asp Pro
    290                 295                 300

Gln Val Asp Arg Leu Leu Asn Glu Ala Val Ala His Arg Arg Pro Thr
305                 310                 315                 320

Tyr Arg Ala His Val Ala Trp Tyr Arg Ile Ala Asp Gly Cys Ala His
                325                 330                 335

Leu Leu Tyr Phe Ile Glu Tyr Ala Asp Cys Asp Pro Arg Gln Ile Phe
            340                 345                 350

Gly Arg Cys Arg Arg Arg Thr Thr Pro Met Trp Trp Thr Pro Ser Ala
        355                 360                 365

Asp Tyr Met Phe Pro Thr Glu Asp Glu Leu Gly Leu Leu Met Val Ala
    370                 375                 380
```

```
Pro Gly Arg Phe Asn Glu Gly Gln Tyr Arg Arg Leu Val Ser Val Asp
385                 390                 395                 400

Gly Val Asn Ile Leu Thr Asp Phe Met Val Ala Leu Pro Glu Gly Gln
                405                 410                 415

Glu Cys Pro Phe Ala Arg Val Asp Gln His Arg Thr Tyr Lys Phe Gly
            420                 425                 430

Ala Cys Trp Ser Asp Asp Ser Phe Lys Arg Gly Val Asp Val Met Arg
        435                 440                 445

Phe Leu Thr Pro Phe Tyr Gln Gln Pro Pro His Arg Glu Val Val Asn
    450                 455                 460

Tyr Trp Tyr Arg Lys Asn Gly Arg Thr Leu Pro Arg Ala Tyr Ala Ala
465                 470                 475                 480

Ala Thr Pro Tyr Ala Ile Asp Pro Ala Arg Pro Ser Ala Gly Ser Pro
                485                 490                 495

Arg Pro Arg Pro Arg Pro Arg Pro Arg Pro Arg Pro Lys Pro Glu Pro
            500                 505                 510

Ala Pro Ala Thr Pro Ala Pro Pro Gly Arg Leu Pro Glu Pro Ala Thr
        515                 520                 525

Arg Asp His Ala Ala Gly Gly Arg Pro Thr Pro Arg Pro Pro Arg Pro
    530                 535                 540

Glu Thr Pro His Arg Pro Phe Ala Pro Pro Ala Val Val Pro Ser Gly
545                 550                 555                 560

Trp Pro Gln Pro Ala Glu Pro Phe Pro Pro Arg Thr Thr Ala Ala Pro
                565                 570                 575

Gly Val Ser Arg His Arg
            580


<210> SEQ ID NO 15
<211> LENGTH: 37
<212> TYPE: DNA
<213> ORGANISM: Artificial
<220> FEATURE:
<223> OTHER INFORMATION: Primer gBR1

<400> SEQUENCE: 15

gttaccagaa ccacccgagt actcggggca ggcctgc                              37


<210> SEQ ID NO 16
<211> LENGTH: 37
<212> TYPE: DNA
<213> ORGANISM: Artificial
<220> FEATURE:
<223> OTHER INFORMATION: Primer gBF2

<400> SEQUENCE: 16

tcgggtggtt ctggtaacga catgctgagc cgcatcg                              37


<210> SEQ ID NO 17
<211> LENGTH: 60
<212> TYPE: DNA
<213> ORGANISM: Artificial
<220> FEATURE:
<223> OTHER INFORMATION: Primer gBR2

<400> SEQUENCE: 17

ccaagcttct agtgatggtg atggtgatgg tgatgcgtca ggttcagggt cacccgcgtg      60


<210> SEQ ID NO 18
<211> LENGTH: 32
<212> TYPE: DNA
```

<213> ORGANISM: Artificial
<220> FEATURE:
<223> OTHER INFORMATION: Primer gBF

<400> SEQUENCE: 18
aggaattcag acgcgggccg cctcggcctc gc 32

<210> SEQ ID NO 19
<211> LENGTH: 58
<212> TYPE: DNA
<213> ORGANISM: Artificial
<220> FEATURE:
<223> OTHER INFORMATION: Primer gBR

<400> SEQUENCE: 19
ccaagcttct agtgatggtg atggtgatgg tgatggttgt ggtccacctt gaccacgc 58

<210> SEQ ID NO 20
<211> LENGTH: 34
<212> TYPE: DNA
<213> ORGANISM: Artificial
<220> FEATURE:
<223> OTHER INFORMATION: Primer gD18F

<400> SEQUENCE: 20
aggaattcag gcggacgtgg acgccgtgcc cgcg 34

<210> SEQ ID NO 21
<211> LENGTH: 58
<212> TYPE: DNA
<213> ORGANISM: Artificial
<220> FEATURE:
<223> OTHER INFORMATION: Primer gD353R

<400> SEQUENCE: 21
ccaagcttct agtgatggtg atggtgatgg tgatggcggt ggcgcgagac gcccggcg 58

<210> SEQ ID NO 22
<211> LENGTH: 39
<212> TYPE: DNA
<213> ORGANISM: Artificial
<220> FEATURE:
<223> OTHER INFORMATION: Primer GP67F(XhoI)

<400> SEQUENCE: 22
ccgctcgaga tgctactagt aaatcagtca caccaaggc 39

<210> SEQ ID NO 23
<211> LENGTH: 40
<212> TYPE: DNA
<213> ORGANISM: Artificial
<220> FEATURE:
<223> OTHER INFORMATION: Primer HNgD353R(NheI)

<400> SEQUENCE: 23
ctagctagcc tagtgatggt gatggtgatg gcggtggcgc 40

<210> SEQ ID NO 24
<211> LENGTH: 36
<212> TYPE: DNA
<213> ORGANISM: Artificial
<220> FEATURE:
<223> OTHER INFORMATION: Primer gBDR1

<400> SEQUENCE: 24
cgtccacgtc cgccgtcagg ttcagggtca cccgcg 36

-continued

```
<210> SEQ ID NO 25
<211> LENGTH: 34
<212> TYPE: DNA
<213> ORGANISM: Artificial
<220> FEATURE:
<223> OTHER INFORMATION: Primer gBDF2

<400> SEQUENCE: 25

ctgaacctga cggcggacgt ggacgccgtg cccg                              34


<210> SEQ ID NO 26
<211> LENGTH: 23
<212> TYPE: DNA
<213> ORGANISM: Artificial
<220> FEATURE:
<223> OTHER INFORMATION: Primer M13F

<400> SEQUENCE: 26

cccagtcacg acgttgtaaa acg                                          23


<210> SEQ ID NO 27
<211> LENGTH: 23
<212> TYPE: DNA
<213> ORGANISM: Artificial
<220> FEATURE:
<223> OTHER INFORMATION: Primer M13R

<400> SEQUENCE: 27

agcggataac aatttcacac agg                                          23
```

SUBUNIT VACCINE OF PORCINE PSEUDORABIES VIRUS AND PREPARATION METHOD

CROSS-REFERENCE TO RELATED APPLICATIONS

This is the national phase of International Patent Application No. PCT/CN2015/094478, filed 12 Nov. 2015, which claims priority to Chinese Patent Application No. 201510375665.5, filed 29 Jun. 2015. The disclosure of each of these applications is incorporated herein by reference in its entirety for all purposes.

FIELD OF THE INVENTION

This invention relates to a field of veterinary biological products, specifically relates to a subunit vaccine of porcine pseudorabies virus and preparation method thereof, and use in preparing composition for preventing and/or treating diseases associated with porcine pseudorabies virus and infection caused by the porcine pseudorabies virus.

BACKGROUND OF THE INVENTION

Pseudorabies, also called Aujeszky's disease, is an acute infectious disease caused by Suid herpesvirus 1 (SuHV1) belonging to the Alphaherpesvirinae subfamily for many kinds of livestock such as swine, cattle and sheep, as well as poultry and wild animals, with the main symptoms of fever, intense itching (except swine) and encephalomyelitis. Pseudorabies in swine is found nationwide in China causing severe damages, and is one of the major diseases limiting the large-scale production of pig farms. Infection can result in abortion, stillborn or mummified fetuses in pregnant sows, and neurological signs, paralysis and a high death rate in piglets. Pseudorabies virus (PRV) with strong pantropic properties, neurotropic properties and latent infectivity, may establish long-term latent infection in the peripheral nervous system. The latently infected host starts to get sick when the latent virus is activated into the infectious virus.

Practical demand for subunit vaccine of preventing pseudorabies infection with a high expression level and effective immunity is raised in the present field.

SUMMARY OF THE INVENTION

For the very first time, the present disclosure achieves preparation of subunit vaccine by fusion-expression of a fragment obtained from gB protein of porcine pseudorabies virus, the subunit vaccine provides a better protection effect against pseudorabies caused by the porcine pseudorabies virus. Unexpectedly, it is found that the expression level of the prepared gB protein fragment is significantly increased and cost of immunization is greatly reduced.

The present disclosure relates to a porcine pseudorabies virus gB protein fragment, or a conservative variant or active fragment thereof, wherein the gB protein fragment is capable of maintaining antigenic activity of the gB protein, an amino acid sequence of the variant or the active fragment, which has substitution, addition, or deletion of one or several conservative amino acids comparing with an amino acid sequence of the gB protein fragment, is capable of maintaining antigenic activity of the gB protein fragment.

Another aspect of the present disclosure relates to a nucleotide sequence encoding the porcine pseudorabies virus gB protein fragment of the invention, or the conservative variant oractive fragment thereof.

A further aspect of the present disclosure relates to a porcine pseudorabies virus gB-gD protein, wherein the gB-gD protein comprises the gB protein fragment of the invention, or the conservative variant or active fragment thereof, and gD protein.

A further aspect of the present disclosure relates to a subunit vaccine of porcine pseudorabies virus, wherein the subunit vaccine comprises an immune amount of the gB protein fragment of the invention, or the conservative variant oractive fragment thereof and a pharmaceutically acceptable carrier.

The present disclosure further relates to a subunit vaccine of porcine pseudorabies virus, wherein the subunit vaccine comprises an immune amount of the gB-gD protein fragment according to the present invention and a pharmaceutically acceptable carrier.

The present disclosure further relates to a preparation method of a subunit vaccine, wherein the method comprises: 1) a step of cloning a nucleotide sequence of a gB protein fragment of the present disclosure, or a conservative variant or active fragment thereof; 2) a step of expressing the cloned nucleotide sequence of the step 1) to obtain the gB protein fragment present disclosure, or the conservative variant oractive fragment thereof; and 3) a step of preparing the subunit vaccine by adding a pharmaceutically acceptable carrier and an adjuvant to the gB protein fragment, or the conservative variant oractive fragment thereof obtained from the step 2).

The present disclosure further relates to a preparation method of a subunit vaccine, wherein the method comprises: 1) a step of cloning a nucleotide sequence of a gB protein fragment of the present disclosure, or a conservative variant or active fragment thereof and cloning a nucleotide sequence of gD protein; 2) a step of tandem-expressing or fusion-expressing the cloned nucleotide sequences of the step 1) to obtain the gB-gD protein; and 3) a step of preparing a subunit vaccine by adding a pharmaceutically acceptable carrier and an adjuvant to the gB-gD protein obtained from step 2).

The present disclosure further relates to use of a gB protein fragment, or the conservative variant or active fragment thereof, the gB-gD protein, and the subunit vaccine of porcine pseudorabies virus in prepraring a medicine for preventing and/or treating diseases associated with porcine pseudorabies virus and infection caused by the porcine pseudorabies virus.

BRIEF DESCRIPTION OF THE DRAWINGS

FIG. 1 is a homologous alignment of amino acid sequences of gB proteins in the HN1201 strain, Bartha strain, Kaplan strain and Becker strain.

SEQUENCE LISTING

Figure 1A:
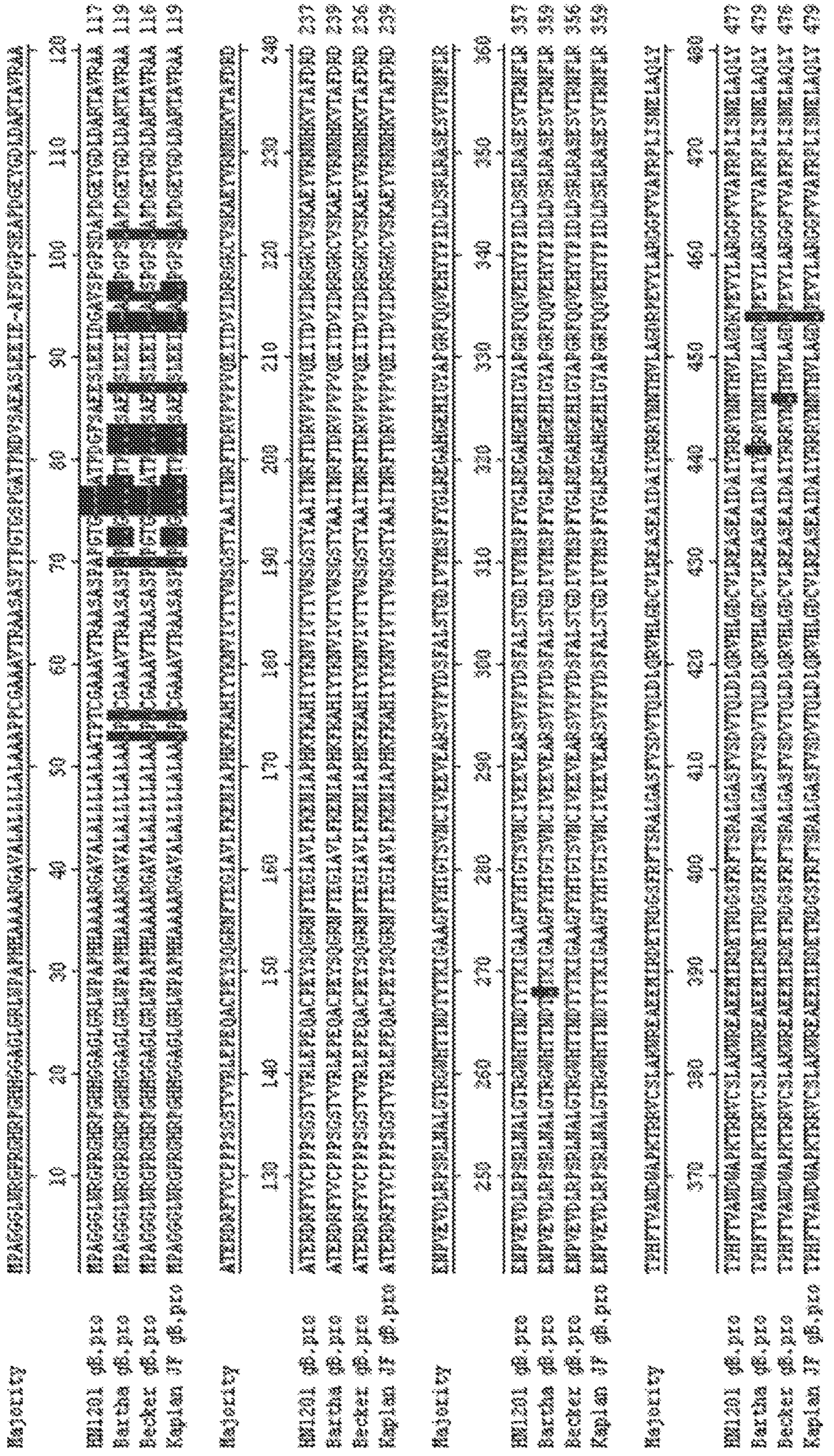
FIG. 1A shows alignment of amino acid sequeces of each gB protein from 1st amino acid residue to about 480th amino acid residue.

SEQ ID NO: 1 is the nucleotide sequence of gB protein in the PRV HN1201 strain.

SEQ ID NO: 2 is the amino acid sequence of gB protein in the PRV HN1201 strain.

SEQ ID NO: 3 is the nucleotide sequence of gB protein fragment in the PRV HN1201 strain.

SEQ ID NO: 4 is the amino acid sequence of gB protein fragment in the PRV HN1201 strain.

SEQ ID NO: 5 is the nucleotide sequence of gB protein fragment in the PRV Bartha strain.

SEQ ID NO: 6 is the amino acid sequence of gB protein fragment in the PRV Bartha strain.

SEQ ID NO: 7 is the nucleotide sequence of gB protein fragment in the PRV Kaplan strain.

SEQ ID NO: 8 is the amino acid sequence of gB protein fragment in the PRV Kaplan strain.

SEQ ID NO: 9 is the nucleotide sequence of gB protein fragment in the PRV Becker strain.

SEQ ID NO: 10 is the amino acid sequence of gB protein fragment in the PRV Becker strain.

SEQ ID NO: 11 is the nucleotide sequence of gD protein in the PRV HN1201 strain.

SEQ ID NO: 12 is the amino acid sequence of gD protein in the PRV HN1201 strain.

SEQ ID NO: 13 is the nucleotide sequence of fusion protein of gB protein fragment and gD protein in the PRV HN1201 strain.

SEQ ID NO: 14 is the amino acid sequence of fusion protein of gB protein fragment and gD protein in the PRV HN1201 strain.

SEQ ID NO. 15 is the nucleotide sequence of a downstream primer gBR1.

SEQ ID NO. 16 is the nucleotide sequence of an upstream primer gBF2.

SEQ ID NO. 17 is the nucleotide sequence of a downstream primer gBR2.

SEQ ID NO. 18 is the nucleotide sequence of an upstream primer gBF.

SEQ ID NO. 19 is the nucleotide sequence of a downstream primer gBR.

SEQ ID NO. 20 is the nucleotide sequence of an upstream primer gD18F.

SEQ ID NO. 21 is the nucleotide sequence of a downstream primer gD353R.

SEQ ID NO. 22 is the nucleotide sequence of an upstream primer GP67F(XhoI).

SEQ ID NO. 23 is the nucleotide sequence of a downstream primer HNgD353R(NheI).

SEQ ID NO. 24 is the nucleotide sequence of a downstream primer gBDR1.

SEQ ID NO. 25 is the nucleotide sequence of an upstream primer gBDF2.

SEQ ID NO. 26 is the nucleotide sequence of an upstream primer M13F.

SEQ ID NO. 27 is the nucleotide sequence of a downstream primer M13R.

SEQ ID NO: 28 is the amino acid sequence of gB protein in the PRV Bartha strain.

SEQ ID NO: 29 is the amino acid sequence of gB protein in the PRV Becker strain.

SEQ ID NO: 30 is the amino acid sequence of gB protein in the PRV Kaplan strain.

SEQ ID NO: 31 is majority obtained from sequence alignment.

DETAILED DESCRIPTION

Examples of the present disclosure are described as follows.

The term "gB protein", also called "gB glycoprotein", belongs to the most conservative glycoprotein in herpesvirus members and has a size about 2.8 kb.

One aspect of the present disclosure relates to a porcine pseudorabies virus gB protein fragment, or a conservative variant or active fragment thereof, wherein by using a sequence of gB protein in PVR HN1201 strain shown in SEQ ID NO: 2 as a reference site, an amino acid sequence of the gB protein fragment comprises a sequence represented by amino acids 62-148 of gB protein and/or a sequence represented by amino acids 546-700 of gB protein, the gB protein fragment is capable of maintaining antigenic activity of the gB protein; an amino acid sequence of the variant or the active fragment thereof which has substitution, addition or deletion of one or several conservative amino acids comparing with the amino acid sequence of the gB protein fragment, is capable of maintaining antigenic activity of the gB protein fragment.

Due to insertion and deletion of amino acid sites taking place in sequences of gB protein of different porcine pseudorabies viruses, sequence position of the gB protein fragment according to the present disclosure may vary in sequences of gB protein with different porcine pseudorabies virus strains. For example, the corresponding sequence position in porcine pseudorabies virus Bartha strain is at amino acids 62-150 (ie, 62nd amino acid to 150 th amino acid) and amino acids 548-702 of the gB protein, the corresponding sequence position in porcine pseudorabies virus Kaplan strain is at amino acids 62-154 and amino acids 552-706 of the gB protein, the corresponding sequence position in porcine pseudorabies virus Becker strain is at amino acids 62-147 and amino acids 545-699 of the gB protein. By comparing with the sequence of gB protein in PVR HN1201 strain of SEQ ID NO: 2, a sequence that is corresponding to a sequence represented by amino acids 62-148 and amino acids 546-700 of the gB protein in PVR HN1201 strain is the gB protein fragment sequence of the present disclosure.

Figure 1B:
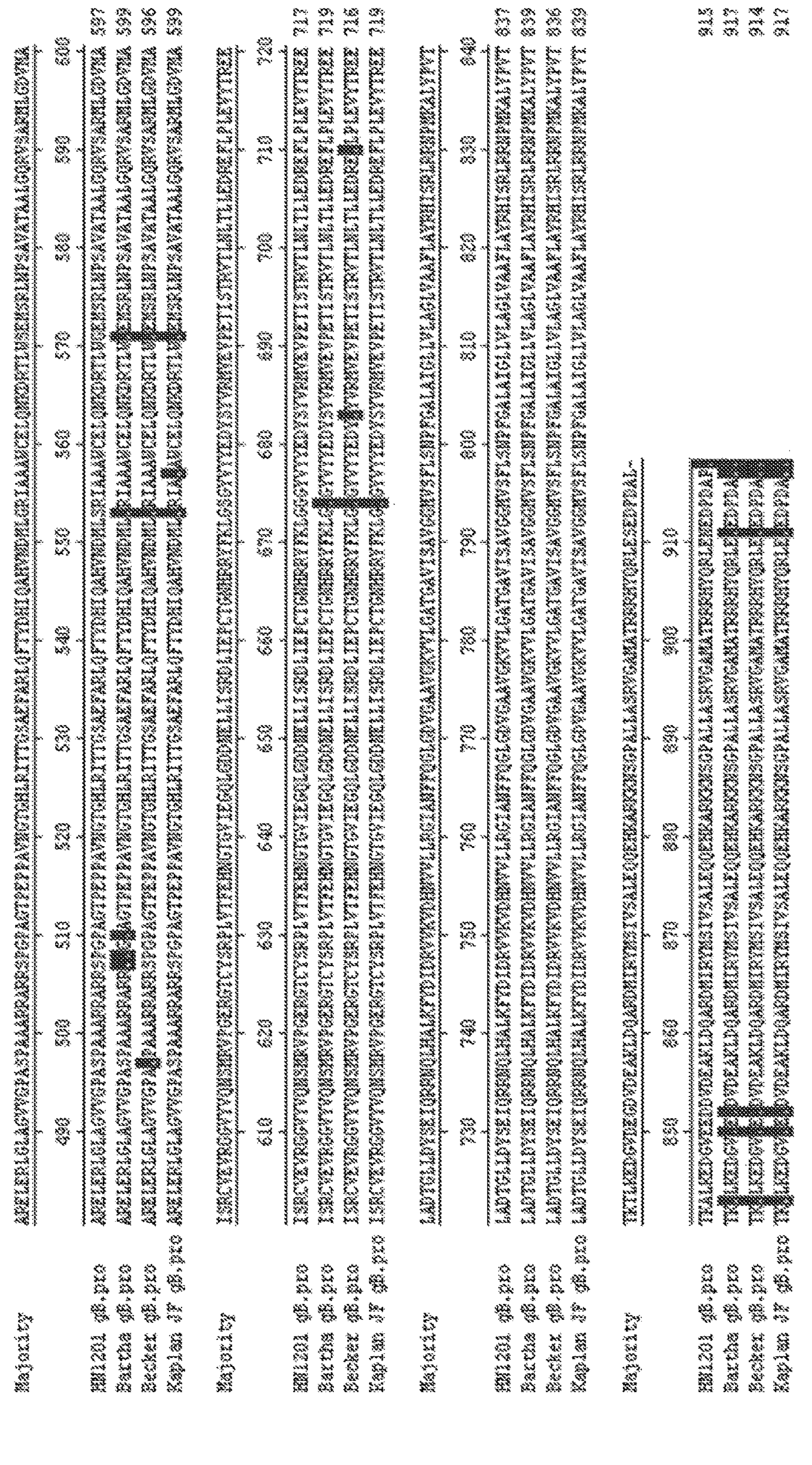
FIG. 1B shows alignment of amino acid sequences of each gB protein from about 481th acid residue to the end.

Amino acid sites of the gB protein fragment in the gB protein sequence can be compared by DNAStar so as to determine the corresponding sites to the gB protein fragment amino acid sequence of the present disclosure in the sequences of different porcine pseudorabies virus strains. The result of amino acid site alignment among the porcine pseudorabies virus gB protein fragments of HN1201 strain, Bartha strain, Kaplan strain and Becker strain is shown in FIG. 1. The sequence alignment can also be performed by other biological software such MEGA, DNAman, clustalX, bioedit, Vestor NTI software, and blastin NCBI, so as to determine the corresponding sites to the gB protein fragment amino acid sequence of the present disclosure in the sequences of different porcine pseudorabies virus strains.

The term "conservative variant" in the present disclosure refers to a variant that remains its parental characteristics such as basic immunological characteristics, structural characteristics, regulating characteristics or biochemical characteristics. In general, an amino acid sequence of a conservative variant of a polypeptide is different from the parent polypeptide. But the difference is finite so that the parent polypeptide sequence is very similar to the conservative variant as a whole and is the same in many regions. The difference between the conservative variant and the parent polypeptide amino acid sequence may be, for example, substitution, addition and deletion of one or several amino acid residues or any combination thereof. Substituted or inserted amino acid residues may be encoded by genetic codes or may not be encoded by genetic codes. The conservative variant of the polypeptide may be generated naturally or unnaturally. The unnaturally generated conservative variant of the polypeptide may be produced by induced mutation technique or direct synthesis.

The amino acid sequence of the variant and the active fragment according to the present disclosure, which has substitution, addition, or deletion of one or several conservative amino acids comparing with the amino acid sequence of the gB protein fragment, is capable of maintaining antigenic activity of the gB protein fragment, where in the substitution, addition, or deletion of one or several conservative amino acids is meant to be substitution, addition, or deletion of 1-10 conservative amino acids, preferably substitution, addition, or deletion of 1-5 conservative amino acid. The conservative amino acid substitution, addition, or deletion is meant to be the substitution, addition, or deletion with similar property and size, including but not limited to a substitution between glycine and alanine, addition or deletion of glycine or alanine, a substitution between serine and threonine, and a substitution between arginine and lysine.

As one example of the present disclosure, the porcine pseudorabies virus gB protein fragment of the present disclosure, or the conservative variant or active fragment thereof, wherein using a sequence of gB protein in PVR HN1201 strain of SEQ ID NO:2 as a reference site, an amino acid sequence of the gB protein fragment comprises a sequence represented by amino acids 62-148 of gB protein and/or a sequence represented by amino acids 546-700 of gB protein, the gB protein fragment is capable of maintaining antigenic activity of the gB protein; an amino acid sequence of the variant or the active fragment thereof having substitution, addition or deletion of one or several conservative amino acids, comparing with the amino acid sequence of the gB protein fragment is capable of maintaining antigenic activity of the gB protein fragment.

As one example of the present disclosure, the gB protein fragment in the vaccine composition of the present disclosure is from a strain selected from a group comprising PRV JS-2012 strain, PRV HeN1 strain, NVDC-PRV-BJ strain, NVDC-PRV-HEB strain, NVDC-PRV-SD strain, PRV TJ strain, PRV-ZJ01 variant strain, PRV HN1201 variant strain, PRV Fa strain, PRV Bartha strain, PRV Kaplan strain, and PRV Becker strain.

PRV Js-2012 strain has been disclosed in Identification and Characterization of a pseudorabies virus isolated from a dead piglet born to vaccinated sow [J]. Chinese Journal of Animal infectious diseases. 2013, 21(3): 1-7) by Tong Wu, Zhang Qingzhan, Zheng Hao et al. PRV HeN1 strain has been deposited in the China General Microbiological Culture Collection Center on May 20, 2013, of which the accession number is CGMCC NO. 6656 and has been disclosed in the patent application CN102994458A. NVDC-PRV-BJ strain, NVDC PRV-HEB strain and NVDC-PRV-SD strain has been disclosed in Pathogenic Pseudorabies Virus, China, 2012 Emerging Infectious Diseases, Vol. 20, No. 1, January 2014 by Xiuling Yu, Zhi Zhou, Dongmei Hu, et al. PRV TJ strain has been disclosed in A novel gE-deleted pseudorabies virus (PRV) provides rapid and complete protection from lethal challenge with the PRV variant emerging in Bartha-K61-vaccinated swine population in China. Vaccine. 32 (2014) 3379-3385 by Chun-Hua Wang Jin Yuan, Hua-Yang Qin1, et al. A variant strain of pseudorabies virus PRV-ZJ01 has been deposited with an accession number CGMCC No. 8170 and has been disclosed in CN103627678A. PRV HN1201 strain (pseudorabies virus, strain HN1201) has been deposited in the China Center for Type Culture Collection on May 20, 2013, of which the accession number is CCTCC NO. V 201311 and the address is Wuhan University, Wuhan, China. PRV HN1202 strain (pseudorabies virus, strain HN1202) has been deposited in the China Center for Type Culture Collection on Aug. 26, 2013, of which the accession number is CCTCC NO. V 201335 and the address is Wuhan University, Wuhan, China. PRV Fa strain has been disclosed in Clone and sequence analysis of gB, gC, gD genes of pseudorabies virus strain Fa [J], Fujian Journal of Agricultural Sciences, 2007, 22(2): 120-125 by Chen Zhen-hai, et al. PRV Bartha strain and PRV Becker strain have been disclosed in A wide extent of inter-strain diversity in virulent and vaccine strains of alpha herpesviruses, PLoS Pathog. 2011 October; 7(10):e1002282 by Szpara, M. L., et al. PRV Kaplan strain has been disclosed in Analysis of viral and cellular factors influencing herpesvirus-induced nuclear envelope breakdown, J Virol. 2012 January; 86(12):6512-6521 by Grimm, K. S., et al.

As one example of the present disclosure, in the porcine pseudorabies virus gB protein fragment of the present disclosure, or the conservative variant or active fragment thereof, the gB protein fragment comprises a sequence represented by amino acids 62-148 of gB protein in PRV HN1201 strain and/or a sequence represented by amino acids 546-700 of gB protein in PRV HN1201 strain.

As one preferred example of the present disclosure, the amino acid sequence of the gB protein fragment in the porcine pseudorabies virus gB protein fragment of the present disclosure, or the conservative variant or active fragment thereof, is an amino acid sequence of SEQ ID NO: 4.

As one preferred example of the present disclosure, the amino acid sequence of the gB protein fragment in the porcine pseudorabies virus gB protein fragment of the present disclosure, or the conservative variant or active fragment thereof, is encoded by a nucleotide sequence of SEQ ID NO: 3.

As one example of the present disclosure, the gB protein fragment in the porcine pseudorabies virus gB protein fragment of the present disclosure, or the conservative variant or active fragment thereof, comprises a sequence represented by amino acids 62-150 of gB protein in PRV Bartha strain and/or a sequence represented by amino acids 548-702 of gB protein in PRV Bartha strain.

As one preferred example of the present disclosure, the amino acid sequence of the gB protein fragment in present disclosure the porcine pseudorabies virus gB protein fragment of the present disclosure, or the conservative variant or active fragment thereof, is an amino acid sequence of SEQ ID NO: 6.

As one preferred example of the present disclosure, the amino acid sequence of the gB protein fragment in present disclosure the porcine pseudorabies virus gB protein fragment of the present disclosure, or the conservative variant or active fragment thereof, is encoded by a nucleotide sequence of SEQ ID NO: 5.

As one example of the present disclosure, the gB protein fragment in present disclosure the porcine pseudorabies virus gB protein fragment of the present disclosure, or the conservative variant or active fragment thereof, comprises a sequence represented by amino acids 62-154 of gB protein in PRV Kaplan strain and/or a sequence represented by amino acids 552-706 of gB protein in PRV Kaplan strain.

As one preferred example of the present disclosure, the amino acid sequence of the gB protein fragment in present disclosure the porcine pseudorabies virus gB protein fragment of the present disclosure, or the conservative variant or active fragment thereof, is an amino acid sequence of SEQ ID NO: 8.

As one preferred example of the present disclosure, the amino acid sequence of the gB protein fragment in present disclosure the porcine pseudorabies virus gB protein fragment of the present disclosure, or the conservative variant or active fragment thereof, is encoded by a nucleotide sequence of SEQ ID NO: 7.

As one preferred example of the present disclosure, the gB protein fragment in present disclosure the porcine pseudorabies virus gB protein fragment of the present disclosure, or the conservative variant or active fragment thereof, comprises a sequence represented by amino acids 62-147 of gB protein in PRV Becker strain and/or a sequence represented by amino acids 545-699 of gB protein in PRV Becker strain.

As one preferred example of the present disclosure, the amino acid sequence of the gB protein fragment in present disclosure the porcine pseudorabies virus gB protein fragment of the present disclosure, or the conservative variant or active fragment thereof, is an amino acid sequence of SEQ ID NO: 10.

As one preferred example of the present disclosure, the amino acid sequence of the gB protein fragment in present disclosure the porcine pseudorabies virus gB protein fragment of the present disclosure, or the conservative variant or active fragment thereof, is encoded by a nucleotide sequence of SEQ ID NO: 9.

The term "gD protein", also called "gD glycoprotein", is a structural protein that is necessary for infection of porcine pseudorabies virus and is one of the major glycoproteins on the surface of envelopes of mature viral particles, also known as "gp50 protein".

An aspect of the present disclosure relates to a porcine pseudorabies virus gB-gD protein, wherein the gB-gD protein comprises the gB protein fragment of the present disclosure, or the conservative variant or active fragment thereof, and gD protein.

As one example of the present disclosure, the gB protein, or the conservative variant or active fragment thereof, is tandem-expressed or fusion-expressed with the gD protein.

As one example of the present disclosure, an amino acid sequence of the gD protein in the porcine pseudorabies virus gB-gD protein of the present disclosure is an amino acid sequence of SEQ ID NO: 12.

As one preferred example of the present disclosure, the amino acid sequence of the gD protein in the porcine pseudorabies virus gB-gD protein of the present disclosure is encoded by an nucleotide sequence of SEQ ID NO: 11.

As one preferred example of the present disclosure, in the porcine pseudorabies virus gB-gD protein of the present disclosure, an amino acid sequence of the gB protein fragment is an amino acid sequence of SEQ ID NO:4, an amino acid sequence of the gD protein is an amino acid sequence of SEQ ID NO: 12.

As one of the most preferred examples of the present disclosure, the gB protein fragment and the gD protein in the porcine pseudorabies virus gB-gD protein of the present disclosure is a fusion protein, of which the amino acid sequence is represented as SEQ ID NO: 14.

As one of the most preferred examples of the present disclosure, the gB protein fragment and the gD protein in the porcine pseudorabies virus gB-gD protein of the present disclosure is a fusion protein, of which an nucleotide sequence is represented as SEQ ID NO: 13.

A further aspect of the present disclosure relates to a subunit vaccine of porcine pseudorabies virus, wherein the subunit vaccine comprises an immune amount of the gB protein fragment of the present disclosure, or the conservative variant or active fragment thereof, and a pharmaceutically acceptable carrier.

As one example of the present disclosure, content of the gB protein, or the conservative variant or active fragment thereof in the subunit vaccine is 25-100 μg/ml.

As one example of the present disclosure, the subunit vaccine comprises an adjuvant.

As one example of the present disclosure, the porcine pseudorabies virus subunit vaccine of the present disclosure comprises the gB protein fragment, which is an amino acid sequence of SEQ ID NO: 4 of the present disclosure, in a content of 25-100 μg/ml.

As an example of the present disclosure, in the porcine pseudorabies virus subunit vaccine of the present disclosure, the gB protein fragment of amino acid sequence of SEQ ID NO: 6, SEQ ID NO: 8, or SEQ ID NO: 10 of the present disclosure can also be selected to replace the gB protein fragment of the amino acid sequence of SEQ NO: 4.

The gB protein fragment and the gD protein included in the subunit vaccine composition for preventing and/or treating the infection caused by the porcine pseudorabies virus according to the present disclosure, can also be polypeptides of amino acid sequences that are substantially the same as the functional derivatives thereof.

The term "functional derivatives" refers to a protein/peptide sequence that has a functional biological activity substantially similar to a biological activity of an intact protein/peptide sequence. In other words, it preferably refers to a peptide or a fragment thereof that substantially retains the ability to elicit an immune response, such as a protective response against an attack of porcine pseudorabies virus strain, when the function derivative is administered to an animal.

The term "nucleotide sequence" refers to such a polynucleotide sequence that is a separated part of the nuclei acid of the present disclosure constructed artificially (e.g., by chemical synthesis) or by cleavage of a natural product into multiple small fragments (using restriction endonucleases or mechanical shearing), or a part of nuclei acid synthesized by PCR, DNA polymerase or any other polymerization technique known in the art, or a nuclei acid part expressed in a host cell by recombinant nucleic acid techniques known to one skilled in the art.

As appreciated and used herein generally, the term "functional fragment" refers to a nucleic acid sequence that encodes a functional biologically active polypeptide/protein that has substantially the same biological activity as an intact nucleic acid sequence. In other words, in the context of the present disclosure, it preferably refers to a nucleic acid or a fragment thereof that substantially retains the ability to encode such polypeptides/protein, which, when administered to an animal, elicits immune response and a preferred protective response against an attack of porcine pseudorabies virus.

When referring to an amino acid sequence, "substantially the same" can be understood that the polypeptides of the present disclosure preferably have such an amino acid sequence which has at least 70% homology to some or all of the sequences represented in SEQ ID: 4, preferably 80%, more preferably 90%, most preferably 95%.

As used herein, the term "homology" also includes being the same or similar as the reference sequence, while providing a simple substitution/modification of any amino acid. The homology search for this aspect can be performed by using BLAST-P (Basic Local Alignment Search Tool), a program known to one skilled in the art. For the corresponding nucleic acid sequence, homology relates to BLASTX and BLASTN software known in the art.

The level of amino acid sequence homology or nucleotide sequence homology is limited such that the change of the sequence does not affect autoimmunity.

The term “adjuvant” refers to a substance that is added to the composition of the present disclosure for increasing immunogenicity of the composition. The known adjuvants include, but are not limited to, oil adjuvants, water soluble adjuvants, aluminum salt adjuvants, cytokine adjuvants.

As used herein, the term “oil adjuvant”, also known as “oily adjuvant” or “oil emulsion adjuvant”, consists of one or more of vegetable oil, animal oil and mineral oil, and is used for extending the retention time of an immunogen in the body such that the immunogen is released slowly and sustainably, and thereby to enhance phagocytosis and bactericidal ability of a macrophage.

As used herein, the term “water soluble adjuvant”, also known as “water based adjuvant” or “water adjuvant”, is a water soluble dispersion of a polymer for improving the efficacy and safety of water soluble vaccine, and can be composed of synthetic polyacrylic acid polymers with high molecular weight.

As used herein, the term “aluminum salt adjuvant”, also known as “alhydrogel adjuvant” or “aluminum adjuvant”, of which primary function is achieving slow release while having activating effect to immune cells, includes aluminum hydroxide adjuvants and aluminum phosphate adjuvants. When an antigen is mixed with aluminum hydroxide or aluminum phosphate before injection, the antigen can be stored in the injection site so as to achieve slow release of the antigen and non-specific immune stimulating effect.

As used herein, the term “cytokine adjuvant” including IL-1, IL-2, IL-3, IL-4, IL-5, IL-6, IL-7, IL-10, IL-12, IL-15, IL-18, INF-γ, GM-CSF, TNF-α, TNF-β, TCA-3 and like, also known as “cytokine” or “cellular factor”, is a class of non-immune globulins, local natural proteins or glycoproteins that are secreted by a host cell of a living body, arrive at other cells of the host by diffusion, inter-cellular contact or blood circulation, and act at very low concentrations in body fluids. It also collectively refers to a class of highly active and multi-functional small molecular proteins, which is generated and secreted by immune cells activated by the body and some non-immune cells and is capable of regulating cell growth and differentiation and closely related to hematopoiesis, inflammation, and immune response and like. The cytokine adjuvant is capable of eliciting or inhibiting immunity, enhancing cell differentiation and regulating physiological function of cells and inter-cellular information transmission in the immune response system, plays a very important role of regulation in the immune system.

Among oil adjuvants, a type of 206 adjuvant is used in the examples of the present disclosure.

The amount of adjuvant that is suitable for the composition of the present disclosure is preferably an effective amount. The “effective amount” refers to a required amount of the adjuvant that is necessary or sufficient to have a immunological effect in the host in combination with the antigen of the invention without causing excessive side effects. The precise amount of adjuvant to be administrated will vary depending on factors such as the components employed and the type of diseases being treated, the type and age of the animal to be treated, the mode of administration, and other components in the composition.

The amount of components or constituents of the composition of the present disclosure is preferably an therapeutically effective amount. The “therapeutically effective amount” refers to a required amount of the composition that have a immunological effect in the host employed without causing excessive side effects. The components being used and the precise amount of composition to be administrated will vary depending on factors such as the type of diseases being treated, the type and age of the animal to be treated, the mode of administration, and other components in the composition.

As another aspect of the present disclosure relates to a subunit vaccine of porcine pseudorabies virus, wherein the subunit vaccine comprises an immune amount of the gB-gD protein of the invention and a pharmaceutically acceptable carrier.

As one example of the present disclosure, content of the gB-gD protein is 25-100 μg/ml.

As one example of the present disclosure, the subunit vaccine comprises an adjuvant.

As one example of the present disclosure, the porcine pseudorabies virus subunit vaccine present disclosure comprises tandem-expressed gB protein fragment of the amino acid sequence of SEQ ID NO: 4 of the present disclosure and gD protein of the amino acid sequence of SEQ ID NO: 12 according to the present disclosure, the content of the protein antigen is 25-100 μg/ml.

As an example of the present disclosure in the tandem-expressed porcine pseudorabies virus subunit vaccine of the present disclosure the gB protein fragment of amino acid sequence of SEQ ID NO: 6, SEQ ID NO: 8, or SEQ ID NO: 10 can also be selected to replace the gB protein fragment of the amino acid sequence of SEQ NO: 4.

As one example of the present disclosure, the porcine pseudorabies virus subunit vaccine of the present disclosure comprises a fusion-expressed gB protein fragment of the amino acid sequence of SEQ ID NO: 4 present disclosure and gD protein of the amino acid sequence of SEQ ID NO: 12 according to the present disclosure, the content of the protein antigen is 25-100 μg/ml.

As an example of the present disclosure, in the fusion-expressed porcine pseudorabies virus subunit vaccine of the present disclosure, the gB protein fragment of amino acid sequence of SEQ ID NO: 6, SEQ ID NO: 8, or SEQ ID NO: 10 can also be selected to replace the gB protein fragment of the amino acid sequences of SEQ NO: 4.

The present disclosure further relates to a preparation method of a subunit vaccine, wherein the method comprises: 1) a step of cloning a nucleotide sequence of a gB protein fragment of the present disclosure, or a conservative variant or active fragment thereof; 2) a step of expressing the cloned nucleotide sequence of the step 1) to obtain the gB protein fragment present disclosure, or the conservative variant or active fragment thereof; and 3) a step of preparing a subunit vaccine by adding a pharmaceutically acceptable carrier and an adjuvant to the gB protein fragment, or the conservative variant or active fragment thereof obtained from the step 2).

As one example of the present disclosure, in the preparation method of the subunit vaccine of the present disclosure, an amino acid sequence of the gB protein fragment is an amino acid sequence of SEQ ID NO: 4, SEQ ID NO: 6, SEQ ID NO: 8, or SEQ ID NO: 10.

The present disclosure further relates to a preparation method of a subunit vaccine, wherein the method comprises: 1) a step of cloning a nucleotide sequence of a gB protein fragment of the present disclosure, or a conservative variant or active fragment thereof and cloning a nucleotide sequence of gD protein; 2) a step of tandem-expressing or fusion-expressing the cloned nucleotide sequences of the step 1) to obtain the gB-gD protein; and 3) a step of preparing a subunit vaccine by adding a pharmaceutically acceptable carrier and an adjuvant to the gB-gD protein obtained from the step 2).

As one example of the present disclosure, in the preparation method of the subunit vaccine of the present disclosure, the expressed gB-gD protein is tandem-expressed gB protein fragment of an amino acid sequence of SEQ ID NO: 4, SEQ ID NO: 6, SEQ ID NO: 8, or SEQ ID NO: 12, and gD protein of an amino acid sequence of SEQ ID NO: 12.

As one example of the present disclosure, in the preparation method of the subunit vaccine of the present disclosure, the expressed gB-gD protein is a fusion-expressed gB protein fragment of an amino acid sequence of SEQ ID NO: 4, SEQ ID NO: 6, SEQ ID NO: 8, or SEQ ID NO: 12, and gD protein of an amino acid sequence of SEQ ID NO: 12.

Another aspect of the present disclosure relates to use of the gB protein fragment, or the conservative variant or active fragment thereof in preparing a medicine for preventing and/or treating diseases associated with porcine pseudorabies virus and infection caused by the porcine pseudorabies virus.

The present disclosure further relates to use of the gB-gD protein in preparing a medicine for preventing and/or treating diseases associated with porcine pseudorabies virus and infection caused by the porcine pseudorabies virus.

The present disclosure further relates to use of the porcine pseudorabies virus subunit vaccine in preparing a medicine for preventing and/or treating diseases associated with porcine pseudorabies virus and infection caused by the porcine pseudorabies virus.

The term "preventing" refers to all behaviors that inhibit PRV infection or delay onset of the disease via administrating the vaccine composition of the present disclosure. The term "treating" refers to all behaviors that alleviate or ameliorate symptoms caused by the PRV infection via administrating the vaccine composition of the present disclosure.

A porcine pseudorabies virus polypeptide related to the present disclosure advantageously stimulates a protective response in animals. In particular, the polypeptide related to the present disclosure comprises substantially the same amino acid sequence as the functional derivative thereof.

The term "protective response" means to prevent PRV associated diseases or infection caused by PRV, or to alleviate severity caused by such diseases.

As used herein, the term "PRV associated diseases" refers to diseases caused by infection of porcine pseudorabies virus. Examples include, but are not limited to, significant neurological signs, lethargy, crying, vomiting, diarrhea and fever in infected piglets, and abortion, mummified or stillborn fetuses or reproductive disorder in infected pregnant sows. Once onset, it can result in abortion, mummified fetuses or stillborn in pregnant sows.

As used herein, the term "PRV associated diseases" further refers to diseases with significant manifestations including but not limited to infection among swine at any ages, horizontal transmission among swine herds, short incubation period (1-2 days), morbidity rates between 10%-100%, mortality rate in pigs between 10%-100% (mortality rate in piglets can reach up to 100%), high fever of pigs after being infected (40° C.~42° C., lasting for more than 3 days), dyspnea, diarrhea, wheezing, coughing, sneezing, hind limb paralysis, dog sitting, suddenly falling down, convulsions, lying on their sides, opisthotonus, making strokes with their arms, and finally dying of exhaustion, and reproductive disorder symptoms caused by infection such as declined semen quality of boar, as well as abortion of pregnant sow (the abortion rate can reach up to 35%), premature birth, stillbirth, weakened piglets (weakened piglets die by 14 days of age), etc. The differences between above described symptoms and symptoms caused by infection of regular pseudorabies virus in the prior art are: in adult pigs (whose weight is above 50 kg), high fever of infected pigs (40° C.~42° C., lasting for more than 3 days), dyspnea, diarrhea, wheezing, coughing, sneezing, hind limb paralysis, dog sitting, suddenly falling down, convulsions, lying on their sides, opisthotonus, making strokes with their arms, and finally dying of exhaustion; sudden incidence of pseudorabies in newborn piglets and piglets below the age of 4 weeks, further resulting in massive death with a mortality of more than 90%; main manifestations in infected piglets including increased body temperature over 41° C., completely loss of appetite, obvious neurological signs and diarrhea; and in piglets just before or after being weaned, mainly respiratory symptoms, such as dyspnea, coughing and runny noses, etc.

The present disclosure has the following outstanding advantages:

(1) The vaccine composition of the present disclosure can be synthesized and expressed abundantly via genetic engineering means or artificial synthesis means, this can not only shorten the time consumed, but also facilitate mass production.

(2) The combination of multi-immunogenic antigens in the porcine pseudoravies virus vaccine of the present disclosure can induce a synergistic immune effect, such that it not only has a better immune effect, but also further reduce the immunization dose and thus the cost of immunization.

(3) The vaccine composition of the present disclosure can effectively protect pigs against the infection of porcine pseudorabies virus, provides a way to improve the prevention and/or treatment of PRV infection and avoids risks of the traditional live vaccine, which are virulence enhancement and virus expansion, it has a positive and practical significance for purifying PRV.

The description of the present disclosure is further provided as follows with reference to the specific examples, and features and advantages of the present disclosure will become more apparent from the following description. However, these examples are only exemplary, but not forming any limitation to the scope of the present disclosure. It should be understood by a person skilled in the art that modifications or alternatives to details and forms of the technical solution of the present disclosure without deviation from the spirit and scope of the present disclosure will be allowed, while those modification and alternatives should all fall within the scope of the present disclosure.

Example 1 Example Preparation of a gB Protein Fragment of Porcine Pseudorabies Virus 1. Gene Amplification of a gB Protein Fragment of Porcine Pseudorabies Virus The PRV HN1201 virus was inoculated on the well-grown PK15 cells and 200 μL of the harvested virus solution was taken. The PRV genomic DNA was extracted according to the instruction of Geneaid Inc.'s viral nucleic acid extraction kit II. gB gene 62-148aa was amplified by using primers gBF and gBR1, gB gene 546-700aa was amplified by using primers gBF2 and gBR2, then these two were amplified into one by Overlapping PCR and with GGSG link amino acids added therebetween through design of primers. Primers are shown in Table 1, PCR system is shown in Table 2, and PCR reaction conditions are shown in Table 3.

TABLE 1

| Gene amplification primers for gB protein fragment | |
|---|---|
| gene | Primer sequence (5'-3') |
| gB gene 62-148aa | gBF1 (SEQ ID No: 18): AGGAATTC AG ACGCGGGCCGCCTCGGCCTCGC<br>gBR1 (SEQ ID No: 15): gttACCAGAACCACCCGAGTACTCGGGGCAGGCCTGC |
| gB gene 546-700aa | gBF2 (SEQ ID No: 16): tcgGGTGGTTCTGGTAACGACATGCTGAGCCGCATCG<br>gBR2 (SEQ ID No: 17): CCAAGCTTCTAGTGATG-GTGATGGTGATGGTGA TGCGTCAGGTTCAGGGTCACCCGCGTG |

TABLE 2

| PCR system | |
|---|---|
| 2 × PrimeSTAR GC buffer | 25 μL |
| genomic DNA of PRV | 1 μL |
| primers (10 pM) | 1 μL/1 μL |
| dNTPs (2.5 mM) | 4 μL |
| PrimeSTAR (2.5 U/μL) | 0.5 μL |
| $ddH_2O$ | 17.5 μL |

TABLE 3

| PCR reaction conditions | |
|---|---|
| 95□ 2 min | 35 cycles |
| 95□ 10 s | |
| 68□ 1 Kb/min | |
| 68□ 10 min | |

2. Construction of Donor Plasmid

The PCR product amplified in step 1 was recovered by OMEGA gel recovery kit, and the recovery product was digested by both of enzyme EcoR I and enzyme Hind III. Meanwhile, pFastBacI containing a signal peptide was digested by both of enzyme EcoR I and enzyme Hind III. After enzyme digestion, vector of pFastBacI was linked to the PCR product.

The linkage product was transformed into DH5α according to conventional transformation method, and then DH5α was spread onto LB plate containing ampicillin and cultured overnight at 37° C. A single colony was picked and placed in 3-5 mL liquid LB containing ampicillin, cultured at 37° C. and 220 rpm for 12-16 h. Plasmid extraction was performed by following instruction of a plasmid mini kit (purchased from TIANGEN) and identified by enzyme digestion with both of enzyme EcoR I and enzyme Hind III. The plasmid identified correct was named pFastBac-HNgBΔ148~546.

3. Construction of Recombinant Bacmid 1-2 μL of pFastBac-HNgBΔ148~546 plasmid was added to DH10Bac competent cells, flicked and mixed well, incubated on ice for 30 min, heat shocked at 42° C. for 60 s, incubated on ice for 5 min and then added with 400 μl SOC culture medium to be cultured at 37° C. and 200 rpm for 4 h. 100 μL bacteria solution was took and spread on a plate containing IPTG/X-gal/Knamycin/tetracycline/gentamicin, cultured at 37° C. for at least 48 h. When the blue-white bacterial colonies became obvious, a single white colony was picked and placed in 5 mL liquid LB culture medium containing Knamycin/tetracycline/gentamicin, and incubated overnight with shaking. 1 μL of product was picked on the next day as a template for PCR identification. The size of PCR product was the size of a targeted fragment, which is more than 2300 bp. The recombinant Bacmid was extracted with the reagents in the plasmid mini kit (purchased from Tiangen Biotech Co., LTD) and named Bac-HNgBΔ148~546.

4. Acquisition and Passage of a Recombinant Baculovirus

The recombinant Bacmid Bac-HNgBΔ148~546 was transfected into insect cells sf9. The transfection was performed according to the instruction of Cellfectin® II Regent. 72 hours after transfection, when the cells were infected, the supernatant of cell culture was collected and marked as rBac-HNgBΔ148~546 P1.

Sf9 cells at logarithmic growth phase were inoculated on 10 cm cell culture dish at $0.9\times10^6$ cell/dish. After the cells were fully adhered to the wall, the P1 recombinant baculovirus was added to the cell culture dish pre-spread with sf9 cells at a volume ratio of 1:20 to 1:40 and cultured at 27° C., and after about 72 h at which the infection of the cells was obvious, the supernatant was harvested and marked as P2 generation of recombinant baculovirus, which was wrapped with foil and stored in dark at 4° C. refrigerator to be spare. This step was repeated with an inoculation ratio of 1:100 to 1:200 to harvest P3 and P4 generation of recombinant baculovirus.

5. Expression of Proteins

The recombinant virus subcultured to P4 was inoculated into 1 L of Hi5 cells at a volume ratio of 1:5 to 1:10. Cells were harvested about 48 h after inoculation, and supernatant obtained by centrifugation was subjected to Western Blot to confirm that the target protein was expressed. After His affinity chromatography and molecular sieve purification, protein quantification was performed with reference to the BCA protein concentration determination kit from Beyotime Biotechnology, and the results showed that 10 mg of HN gBΔ148~546 proteins could be expressed and obtained per 1 L of cells.

Example 2 Preparation of gB Protein of Porcine Pseudorabies Virus

1. Gene Amplification of gB Gene of Porcine Pseudorabies Virus

Using the PRV genomic DNA extracted in Example 1 as a template, the HNgB gene 62-752aa was amplified by using primers gBF and gBR. Primers are shown in Table 4, PCR system is shown in Table 2, and reaction conditions are shown in Table 3.

TABLE 4

| Amplification primer for gB gene | |
|---|---|
| gene | Primer sequence (5'-3') |
| gB gene 62-752aa | gBF (SEQ ID No: 18): AGGAATTC AG ACGCGGGCCGCCTCGGCCTCGC<br>gBR (SEQ ID No: 19): CCAAGCTTCTACTTGATGGTGATGGTGATGGT GATGGTTGTGGTCCACCTTGACCACGC |

2. Construction of Donor Plasmid

Referring to the method for constructing the donor plasmid in Example 1, the PCR product amplified in step 1 was recovered to construct a donor plasmid, and the correct plasmid after identification was named pFastBac-HNgB.

3. Construction of Recombinant Bacmid

Referring to the construction method of recombinant Bacmid in Example 1, the donor plasmid obtained in step 2 was transformed into DH10Bac, and the correct recombinant Bacmid which was identified by PCR was named Bac-HNgB.

4. Acquisition and Passage of a Recombinant Baculovirus

Referring to the method for Acquisition and passaging the recombinant baculovirus in Example 1, the recombinant Bacmid Bac-HNgB transfected cells identified correct in Step 3 was used for preparing the recombinant baculovirus.

5. Expression of Proteins

The recombinant baculovirus obtained in Step 4 was passaged to P4 generation, and the resultant is inoculated into 2 L Hi5 cells at a volume ratio of 1:5 to 1:10. Cells were harvested 48 h after inoculation, and supernatant obtained by centrifugation was subjected to Western Blot to confirm that the target protein was expressed. After His affinity chromatography and molecular sieve purification, protein quantification was performed with reference to the BCA protein concentration determination kit of Beyotime Biotechnology, and the results showed that 5 mg of HN gB protein could be expressed and obtained by 1 L of cells.

Example 3 Comparison of Expression Quantity of gB Protein Fragment and gB Protein of Porcine Pseudorabies Virus By comparing the expression data of the two proteins in Example 1 and Example 2, it was found that the expression quantity of gB protein fragments was double that of the gB protein under the same culture environment and conditions, indicating that the gB protein fragment selected in the present disclosure is easier to express, and thus it can effectively reduce the cost of immunization, and facilitate to large-scale industrial application.

Example 4 Preparation of a Subunit Vaccine of Porcine Pseudorabies Virus

The gB protein fragment prepared in Example 1 and the gB protein prepared in Example 2 were taken respectively and slowly added to an adjuvant. The addition process is performed with stirring by an emulsifying machine at a speed of 800 rpm for 12 min until well mixed. The resultant, that is PRV vaccine composition, was stored at 4° C. The specific ratios are shown in Table 5.

TABLE 5

Component ratios of PRV subunit vaccine

| | Vaccine 1 | Vaccine 2 | Vaccine 3 | Vaccine 4 |
|---|---|---|---|---|
| gBΔ148~546 (μg/ml) | 25 | 50 | 100 | 0 |
| gB (μg/ml) | 0 | 0 | 0 | 100 |
| 206 adjuvant (V/V %) | 50 | 50 | 50 | 50 |

Example 5 Immunogenicity Test of the Subunit Vaccine of Porcine Pseudorabies Virus 24 21-day-old PRV antibody-negative piglets were randomly divided into 6 groups, 4 pigs per group, that is to say, the piglets in 1-4 groups were injected with corresponding vaccine 1, vaccine 2, vaccine 3, vaccine 4, respectively, and the piglets in group 5 and group 6 were injected with the same amount of PBS, as a single immunization. The piglets were challenged with $2\times10^{8.0}TCID_{50}$/piglet of PRV HN1201 strain on day 28 after immunization. After challenge, clinical signs and body temperature of piglets was determined daily at a fixed time.

The result showed that all piglets in first to fourth immunizing groups were protected and survived finally under such challenge dose and all clinical signs were back to normal after 5 days, yet two piglets in group 5 were dead on the second day after challenge and other two were dead on the third day, with obvious clinical signs, and piglets in group 6 survived with no abnormal signs. Challenge results are shown in Table 6.

TABLE 6

Challenge results of piglets immunized with Pseudorabies virus subunit vaccine

| Group | Immunization way | Immunization dose | Number of piglets | Challenge dose | Number of survival | Protection rate (%) |
|---|---|---|---|---|---|---|
| 1 | subcutaneous inoculation | 2 mL | 4 | $2\times10^{8.0}$ $TCID_{50}$ | 4 | 100 |
| 2 | subcutaneous inoculation | 2 mL | 4 | $2\times10^{8.0}$ $TCID_{50}$ | 4 | 100 |
| 3 | subcutaneous inoculation | 2 mL | 4 | $2\times10^{8.0}$ $TCID_{50}$ | 4 | 100 |
| 4 | subcutaneous inoculation | 2 mL | 4 | $2\times10^{8.0}$ $TCID_{50}$ | 4 | 100 |
| 5 | subcutaneous inoculation | 2 mLPBS | 4 | $2\times10^{8.0}$ $TCID_{50}$ | 0 | 0 |
| 6 | subcutaneous inoculation | 2 mLPBS | 4 | — | 4 | — |

Assessment and judgment of the clinical signs of animals were undertaken without knowledge of the immunization state of all individuals, body temperature elevation data is shown in Table 7. The number of days with elevated body temperature in the pigs was counted and ANOVA analysis was used to compare the effects of the vaccine on variation in body temperature of piglets. The result showed that there was no significant difference in body temperature elevation between vaccine 1, vaccine 2 and vaccine 3 group ($P>0.05$), but the difference between vaccine 1, vaccine 2, vaccine 3 and vaccine 4 was extremely significant ($P<0.01$). By comparing the average number of days with elevated body temperature in immunized piglets, the result showed that average number of days with elevated body temperature in piglets is reduced from 3 days, which is the average number of days with elevated body temperature in piglets immunized by vaccine 4, to 1-1.25 days, which are the average numbers of days with elevated body temperature in piglets immunized by vaccine 1, 2 and 3, with an average decline of 58.3%-66.7%. By comparing the clinical evaluations of imnological efficacy of every vaccine, it could be shown that the immune effects of vaccine 1, vaccine 2 and vaccine 3 are significantly better higher than that of vaccine 4. It was demonstrated that the subunit vaccine of the present disclosure comprising the gB protein fragment is superior in immunogenicity to the subunit vaccine of the gB protein, and further found that the subunit vaccine of the present disclosure comprising the gB protein fragment has a lower antigen content yet can achieve better immune effect. By comparing the impact of vaccines on clinical disease, it was shown that pigs vaccinated with the vaccine composition of the invention have significantly less clinical disease than pigs vaccinated with the subunit vaccine of gB protein.

TABLE 7

Body temperature elevation data of piglets immunized with Pseudorabies virus subunit vaccine

| Group | A (day) | B (day) | C (day) | D (day) | Average (day) |
|---|---|---|---|---|---|
| 1 | 2 | 1 | 1 | 1 | 1.25 |
| 2 | 1 | 1 | 1 | 1 | 1 |
| 3 | 1 | 1 | 1 | 1 | 1 |
| 4 | 3 | 3 | 3 | 3 | 3 |
| 6 | 0 | 0 | 0 | 0 | 0 |

Feeding of the piglets in each experimental group were further studied statistically. The results are shown in Table 8. The feeding amount of piglets was recorded for 7 days, and ANOVA analysis was used to compare the effects of the vaccine on variation in feeding amount of piglets. The result showed that there was no significant difference in feeding amount between vaccine 1, vaccine 2 and vaccine 3 group ($P>0.05$), but the difference between vaccine 1, vaccine 2, vaccine 3 and vaccine 4 was extremely significant ($P<0.01$). By comparing the average number of body temperature elevation days of piglets, the result showed that average number of feeding amount of piglets is increased from 210.86 g, which is that average number of feeding amount of piglets immunized by vaccine 4, to 285.60 g-290.58 g, which are the average numbers of feeding amount of piglets immunized by vaccine 1, vaccine 2 and vaccine 3, with an average increase of 58.3%-66.7%. By comparing the clinical evaluations of imnological efficacy of every vaccine, it could be shown that the immune effects of vaccine 1, vaccine 2 and vaccine 3 are significantly higher than that of vaccine 4. This further demonstrates that the subunit vaccine of the present disclosure comprising the gB protein fragment has a better immune effect than the subunit vaccine of the gB protein.

TABLE 8

Feeding data of piglets immunized with Pseudorabies virus subunit vaccine

| Group | A (g) | B (g) | C (g) | D (g) | Average (g) |
|---|---|---|---|---|---|
| 1 | 291.12 | 288.81 | 292.04 | 287.43 | 289.85 |
| 2 | 280.44 | 275.30 | 298.38 | 288.28 | 285.60 |
| 3 | 295.22 | 289.28 | 287.36 | 290.46 | 290.58 |
| 4 | 215.80 | 210.12 | 208.00 | 209.52 | 210.86 |
| 6 | 288.44 | 290.56 | 287.94 | 296.34 | 290.82 |

Example 6 Preparation of gB Protein Fragments of Porcine Pseudorabies Virus Bartha Strain, Kaplan Strain, and Becker Stain In order to prove whether the immunogenicity of the antigenic sites selected by the PRV gB protein fragment of the present disclosure is universal, the full-length genes of PRV Bartha strain gB protein sequence (Accession No.: AEM63980.1), Kaplan strain gB protein sequence (Accession No.: AFI70792.1) and Becker strain gB protein sequence (Accession No.: AEM64118.1) were synthesized by Sangon Biotech (Shanghai) Co., Ltd. The full lengths of the synthesized gene fragments were 2748 bp, 2760 bp, and 2739 bp respectively. Based on the synthetic gene fragments, gB gene templates of the PRV Bartha strain, Kaplan strain, and Becker strain of the present disclosure were prepared.

Primers were designed respectively to amplify the Bartha strain gB gene 62-150aa and 548-702aa, Kaplan strain gB gene 62-154aa and 552-706aa, Becker strain gB gene 62-147aa and 545-699aa, then for each strain, two gB gene fragments were amplified into one by Overlapping PCR and with GGSG link amino acids added therebetween through design of primers. The gB protein fragments were prepared according to the preparation method in Example 1, after His affinity chromatography and molecular sieve purification, protein quantification was performed with reference to the BCA protein concentration determination kit from Beyotime Biotechnology, and the results showed that 10 mg of Bartha gBΔ150~548 protein, 10 mg of Kaplan gBΔ154~552 protein, and 10 mg of Becker gBΔ147~545 protein could be expressed and obtained by 1 L of cells.

Example 7 Preparation of Subunit Vaccines of Porcine Pseudorabies Virus Bartha Strain, Kaplan Strain, and Becker Stain The subunit vaccines of porcine pseudorabies virus were prepared with Example gB protein fragments of porcine pseudorabies virus Bartha strain, Kaplan strain, and Becker stain prepared in Example 6, according to the preparation method in Example 4. The specific ratios are shown in Table 9.

TABLE 9

Component ratios of Bartha strain, Kaplan strain and Becker strain subunit vaccine

| | Vaccine 5 | Vaccine 6 | Vaccine 7 |
|---|---|---|---|
| Bartha (μg/ml) | 50 | 0 | 0 |
| Kaplan (μg/ml) | 0 | 50 | 0 |
| Becker (μg/ml) | 0 | 0 | 50 |
| 206 adjuvant (V/V %) | 50 | 50 | 50 |

Example 8 Immunogenicity Tests of a Subunit Vaccine of PRV Bartha Strain, Kaplan Strain and Becker Strain 20 21-day-old PRV antibody-negative piglets were randomly divided into 5 groups, 4 pigs per group, that is to say, the piglets in 1-3 groups were injected with corresponding vaccine 5, vaccine 6, and vaccine 7 prepared by Example 7, respectively, and the piglets in group 4 and group 5 injected with corresponding the same amount of PBS, as a single immunization. The challenge was made on 28 days after immunization. The piglets were challenged with $2\times10^{8.0}$TCID$_{50}$/piglet of PRV HN1201 strain on day 28 after immunization. After challenge, clinical signs and body temperature of piglets was determined daily at a fixed time.

The result showed that all piglets in first to third immunizing groups were protected and survived finally under such challenge dose and all clinical signs were back to normal after 5 days, yet two piglets in the group 4 were dead on the second day after challenge and other two were dead on the third day, with obvious clinical signs, and piglets in group 5 survived with no abnormal signs. Challenge results are shown in Table 10.

TABLE 10

Challenge protection results of piglets immunized by Bartha strain, Kaplan strain and Becker strain subunit vaccine

| Group | Immunization way | Immunization dose | Number of piglets | Challenge dose | Mumber of survival | Protection rate (%) |
|---|---|---|---|---|---|---|
| 1 | subcutaneous inoculation | 2 mL | 4 | $2 \times 10^{8.0}$ TCID$_{50}$ | 4 | 100 |
| 2 | subcutaneous inoculation | 2 mL | 4 | $2 \times 10^{8.0}$ TCID$_{50}$ | 4 | 100 |
| 3 | subcutaneous inoculation | 2 mL | 4 | $2 \times 10^{8.0}$ TCID$_{50}$ | 4 | 100 |
| 4 | subcutaneous inoculation | 2 mL PBS | 4 | $2 \times 10^{8.0}$ TCID$_{50}$ | 0 | 0 |
| 5 | subcutaneous inoculation | 2 mL PBS | 4 | — | 4 | — |

Body temperature elevation data is shown in Table 11. After challenge, the average number of days with elevated body temperature in vaccine immunizing group was 1-1.25 days on average, which was lower than the average number of days with elevated body temperature in the gB protein immunized group which was 3 days. By comparing the clinical evaluations of imnological efficacy of every vaccine, it could be shown that the vaccine 5, vaccine 6 and vaccine 7 have a good immune effect, it also proved that the antigenic sites selected by the PRV gB protein fragment of the present disclosure has a good immunogenicity, which is universal.

TABLE 11

Body temperature elevation data of piglets immunized with Bartha strain, Kaplan strain and Becker strain subunit vaccine

| Group | A (day) | B (day) | C (day) | D (day) | Average (day) |
|---|---|---|---|---|---|
| 1 | 1 | 1 | 2 | 1 | 1.25 |
| 2 | 1 | 2 | 1 | 1 | 1.25 |
| 3 | 1 | 1 | 1 | 1 | 1 |
| 5 | 0 | 0 | 0 | 0 | 0 |

Example 9 Tandam Expression of the PRV gB Protein Fragment and gD Protein

1. Construction of Donor Plasmids for and an Expression of the PRV gB Protein Fragment and gD Protein Using nuclei acids of the PRV HN1201 strain extracted in Example 1 as a template, with reference to the PCR system and conditions in Example 1, primers gD18F (SEQ ID No: 20): AGGAATTC AGGCGGACGTGGACGCCGTGC-CCGCG and gD353R (SEQ ID No: 21): CCAAGCT-TCTAGTGATGGTGATGGTGATGGTGATG GCGGTG-GCGCGAGACGCCCGGCG were used, the gD gene was amplified, PCR product was digested by both of enzymes EcoR I+Hind III and linked to the pFastBac I which was digested in the same way, the linked product was transformed into DH5a, the positive plasmid obtained was named pFastBac-HNgD.

PCR was performed by using pFastBac-HNgD as a template with primers GP67F(XhoI) and HNgD353R(NheI), the PCR system and conditions were as described in Example 1. The recovered PCR product was double cut with enzymes XhoI and NheI and linked to the pFastBac-Dual carrier which was also digested in the same way. Positive clones obtained by linkage were labeled as pFastBac-gD.

```
GP67F(XhoI) (SEQ ID No: 22):
ccgctcgagATGCTACTAGTAAATCAGTCACACCAAGGC

HNgD353R(NheI) (SEQ ID No: 23):
CTAgctagcCTAGTGATGGTGATGGTGATGGCGGTGGCGC
```

The pFastBac-HNgBΔ148~546 prepared in Example 1 was recovered by digestion with enzymes BamHI and HindIII and was linked to the pFastBac-gD which was also digested in the same way, the identified positive plasmid is pFastBac-gD-gBΔ148~546.

2. Recombinant Bacmid Construction

2 μL of pFastBac-gD-gBΔ148~546 plasmid was added to DH10Bac competent cells, flicked and mixed well, incubated on ice for 30 min, heat shocked at 42° C. for 60 s, incubated on ice for 5 min and then added with 400 μl SOC culture medium to be cultured at 37° C. and 200 rpm for 4 h. 100 μL bacteria solution was took and spread on a plate containing IPTG/X-gal/Knamycin/tetracycline/gentamicin, cultured at 37° C. for at least 48 h. When the blue-white bacterial colonies became obvious, a single white colony was picked and placed in 5 mL liquid LB culture medium containing Knamycin/tetracycline/gentamicin, and incubated overnight with shaking. 1 μL of product was picked on the next day as a template for PCR bacterial solution identification. The size of PCR product was 2560 bp+. The recombinant Bacmid was extracted with the reagents in the plasmid mini kit (purchased from Tiangen Biotech Co., LTD) and named Bac-HN gD-gBΔ148~546.

3. Acquisition and Passage of a Recombinant Baculovirus

The recombinant Bacmid Bac-HN gD-gBΔ148~546 was transfected into insect cells sf9. The transfection was performed according to the instruction of Cellfectin® II Regent Instruction Manual. 72 hours after transfection, when the cells were infected, the supernatant of cell culture was collected and marked as rBac-HN gD-gBΔ148~546 P1.

Sf9 cells at logarithmic growth phase were inoculated on 10 cm cell culture dish at $0.9\times10^6$ cell/dish. After the cells were fully adhered to the wall, the P1 recombinant baculovirus was added to the sf9 plated cell culture dish at a volume ratio of 1:20 to 1:40 and cultured at 27° C. until 72 h at which the challenge of the cells was obvious. The supernatant was harvested and marked as P2 generation recombinant baculovirus, which was wrapped with foil and stored in dark at 4° C. refrigerator to be spare. This step was repeated with a inoculation ration of 1:100 to 1:200 to harvest P3 and P4 generation of recombinant baculovirus.

4. Expression of Proteins

The recombinant virus passaging to P4 was inoculated into 1 L of Hi5 cells in a volume ratio of 1:5 to 1:10. Productive cells were harvested after 48 h of inoculation, and supernatant of the cells obtained by centrifugation was subjected to Western Blot to confirm that the target protein was expressed. After His affinity chromatography and molecular sieve purification, protein quantification was performed with reference to the BCA protein concentration determination kit from Beyotime Biotechnology, and the results showed that 15 mg of HNgBΔ148~546+gD protein could be expressed and obtained by 1 L of cells.

The HNgBΔ148~546+gD protein of the present disclosure can also express the HNgBΔ148~546 protein fragment and the gD protein respectively, and after purification, the two proteins are mixed to prepare the antigen.

Example 10 Preparation of a Subunit Vaccine of the Tandem-Expressed PRV gB Protein Fragment and gD Protein A subunit vaccine was prepared according to the method of Example 4 by taking the PRV gB protein fragment and gD prepared in Example 9, according to the preparation method in Example 4. The specific ratios are shown in Table 12.

TABLE 12

Component ratios of the subunit vaccine of the tandem-expressed PRV gB protein fragment and gD protein

| | Vaccine 8 | Vaccine 9 | Vaccine 10 |
|---|---|---|---|
| BΔ148~546+ gD (μg/ml) | 25 | 50 | 100 |
| 206 adjuvant (V/V %) | 50 | 50 | 50 |

Example 11 Immunogenicity Test of a Subunit Vaccine of the Tandem-Expressed PRV gB Protein Fragment and gD Protein 20 21-day-old PRV antibody-negative piglets were randomly divided into 5 groups, 4 pigs per group, that is to say, the piglets in 1-3 groups were injected with corresponding vaccine 8, vaccine 9, and vaccine 10 prepared by Example 10, respectively, and the piglets in group 4 and group 5 were injected with the same amount of PBS, as a single immunization. The challenge was made on 28 days after immunization. The piglets were challenged with $2\times10^{8.0}TCID_{50}$/piglet of PRV HN1201 strain on day 28 after immunization. After challenge, clinical signs and body temperature of piglets was determined daily at a fixed time.

The result showed that all piglets in first to third immunizing groups were protected and survived finally under such challenge dose and all clinical signs were back to normal after 5 days, yet two piglets in the group 4 were dead on the second day after challenge and other two were dead on the third day, with obvious clinical signs, and piglets in group 5 survived with no abnormal signs. Challenge results are shown in Table 13.

TABLE 13

Challenge results of piglets immunized with tandem-expressed subunit vaccine

| Group | Immunization way | Immunization dose | Number of piglets | Challenge dose | Number of survival | Projection rate (%) |
|---|---|---|---|---|---|---|
| 1 | subcutaneous inoculation | 2 mL | 4 | $2\times10^{8.0}$ $TCID_{50}$ | 4 | 100 |
| 2 | subcutaneous inoculation | 2 mL | 4 | $2\times10^{8.0}$ $TCID_{50}$ | 4 | 100 |
| 3 | subcutaneous inoculation | 2 mL | 4 | $2\times10^{8.0}$ $TCID_{50}$ | 4 | 100 |
| 4 | subcutaneous inoculation | 2 mL PBS | 4 | $2\times10^{8.0}$ $TCID_{50}$ | 0 | 0 |
| 5 | subcutaneous inoculation | 2 mL PBS | 4 | — | 4 | — |

Body temperation data is shown in Table 14. Vaccine immunization group had a transient increase in body temperature. By comparing the clinical evaluations of imnological efficacy of every vaccine, it could be shown that vaccine 8, vaccine 9 and vaccine 10 have a good immune effect.

TABLE 14

Body temperature data of piglets immunized with tandem-expressed subunit vaccine

| Group | A (day) | B (day) | C (day) | D (day) | Average (day) |
|---|---|---|---|---|---|
| 1 | 1 | 1 | 1 | 0 | 0.75 |
| 2 | 0 | 1 | 0 | 1 | 0.5 |
| 3 | 0 | 1 | 1 | 0 | 0.5 |
| 5 | 0 | 0 | 0 | 0 | 0 |

Example 12 Fusion-Expression of the PRV gB Protein Fragment and gD Protein

1. Construction of Donor Plasmids Fusion-Expressed by the PRV gB Protein Fragment and gD Protein gBΔ148~546 and gD were amplified and obtained respectively by using pFastBac-gBΔ148~546 prepared in Example 1 and pFastBac-gD prepared in Example 9 as templates and using gBF and gBDR1, gBDF2 and gD 353R as primers, these two fragments then were linked together by overlapping PCR via primers gBF and gD 353R. The PCR product was labeled as HNgBΔ148~546/gD. This PCR product was digested by both of enzymes BamHI and HindIII and then linked to the pFastBac I vector which was digested in the same way, the resultant positive plasmid was named pFastBac HNgBΔ148~546/gD.

```
gBF (SEQ ID No: 18):
AGGAATTC AG ACGCGGGCCGCCTCGGCCTCGC

gBDR1 (SEQ ID No: 24):
CGTCCACGTCCGCCGTCAGGTTCAGGGTCACCCGCG

gBDF2 (SEQ ID No: 25):
CTGAACCTGACGGCGGACGTGGACGCCGTGCCCG

gD353R (SEQ ID No: 21):
CCAAGCTTCTAGTGATGGTGATGGTGATGGTGATGGCGG
TGGCGCGAGACGCCCGGCG
```

2. Acquisition of Recombinant Bacmid 1-2 μL of pFastBac HNgBΔ148~546/gD plasmid was transformed into DH10Bac by the transformation method described in Example 1 and was spread on LB plate containing kanamycin/tetracycline/gentamicin, cultured at 37° C. for 48 h or so, then the resultant white colonies was picked and PCR identified by using primers M13F (SEQ ID No: 26): CCCAGTCACGACGTTGTAAAACG and M13R (SEQ ID No: 27): AGCGGATAACAATTTCACACAGG. The Bacmid was extracted with the reagent in the Plasmid Kit from Tiangen Biotech Co., LTD and named Bac-HNgBΔ148~546/gD.

3. Acquisition and Passage of a Recombinant Baculovirus

The recombinant Bacmid Bac-HNgBΔ148~546/gD was transfected into insect cells sf9. The transfection was performed according to the instruction of Cellfectin® II Regent. 72 hours after transfection, when the cells were infected, the supernatant of cell culture was collected and marked as vBac-HN HNgBΔ148~546/gD P1.

Sf9 cells at logarithmic growth phase were inoculated on 10 cm cell culture dish at $0.9\times10^6$ cell/dish. After the cells were fully adhered to the wall, the P1 recombinant baculovirus was added to the sf9 plated cell culture dish pre-spread with sf9 cells at a volume ratio of 1:20 to 1:40 and cultured at 27° C., and after about 72 h at which the infection of the cells was obvious, the supernatant was harvested and marked as P2 generation of recombinant baculovirus, which was wrapped with foil and stored in dark at 4° C. refrigerator to be spare. This step was repeated with a inoculation ration of 1:100 to 1:200 to harvest P3 and P4 generation of recombinant baculovirus.

4. Expression of Proteins

The recombinant virus subcultured to P4 was inoculated into 1 L Hi5 cells at a volume ratio of 1:5 to 1:10. Cells were harvested about 48 h after inoculation, and supernatant obtained by centrifugation was subjected to Western Blot to confirm that the target protein was expressed. After His affinity chromatography and molecular sieve purification, protein quantification was performed with reference to the BCA protein concentration determination kit from Beyotime Biotechnology, and the results showed that 5 mg of HNgBΔ148~546/gD protein could be expressed and obtained by 1 L of cells.

Example 13 Preparation of a Subunit Vaccine of the Fusion-Expressed PRV gB Protein Fragment and gD Protein A subunit vaccine was prepared according to the method of Example 4 with the PRV fusion-expressed protein HNgBΔ148~546/gD prepared in Example 12. The specific ratios are shown in Table 15.

TABLE 15

Component ratios of the subunit vaccine of the fusion-expressed PRV gB protein fragment and gD protein

| | Vaccine 11 | Vaccine 12 | Vaccine 13 |
|---|---|---|---|
| gBΔ148~546/gD (μg/ml) | 25 | 50 | 100 |
| 206 adjuvant (V/V %) | 50 | 50 | 50 |

Example 14 Immunogenicity Test of a Subunit Vaccine of the Fusion-Expressed PRV gB Protein Fragment and gD Protein 20 21-day-old PRV antibody-negative piglets were randomly divided into 5 groups, 4 pigs per group, that is to say, the piglets in 1-3 groups were injected with corresponding vaccine 11, vaccine 12, and vaccine 13 prepared by Example 13, respectively, and piglets in group 4 and group 5 were injected with the same amount of PBS, as a single immunization. The challenge was made on 28 days after immunization. The piglets were challenged with $2\times10^{8.0}TCID_{50}$/piglet of PRV HN1201 strain on day 28 after immunization. After challenge, clinical signs and body temperature of piglets was determined daily at a fixed time.

The result showed that all piglets in first to third immunizing groups were protected and survived finally under such challenge dose and all clinical signs were back to normal after 5 days, yet two piglets in the group 4 were dead on the second day after challenge and other two were dead on the third day, with obvious clinical signs, and piglets in group 5 survived with no abnormal signs. Challenge results are shown in Table 16.

TABLE 16

Challenge results of piglets immunized with fusion-expressed subunit vaccine

| Group | Immunization way | Immunization dose | Number of piglets | Challenge dose | Number of survival | Protection rate (%) |
|---|---|---|---|---|---|---|
| 1 | subcutaneous inoculation | 2 mL | 4 | $2 \times 10^{8.0}$ $TCID_{50}$ | 4 | 100 |
| 2 | subcutaneous inoculation | 2 mL | 4 | $2 \times 10^{8.0}$ $TCID_{50}$ | 4 | 100 |
| 3 | subcutaneous inoculation | 2 mL | 4 | $2 \times 10^{8.0}$ $TCID_{50}$ | 4 | 100 |
| 4 | subcutaneous inoculation | 2 mL PBS | 4 | $2 \times 10^{8.0}$ $TCID_{50}$ | 0 | 0 |
| 5 | subcutaneous inoculation | 2 mL PBS | 4 | — | 4 | — |

Body temperature data is shown in Table 17. Vaccine immunization group had a transient increase in body temperature. By comparing the clinical evaluations of imnological efficacy of every vaccine, it could be shown that vaccine 11, vaccine 12 and vaccine 13 have a good immune effect.

TABLE 17

Body temperature data of piglets immunized with fusion-expressed subunit vaccine

| Group | A (day) | B (day) | C (day) | D (day) | Average (day) |
|---|---|---|---|---|---|
| 1 | 1 | 0 | 1 | 1 | 0.75 |
| 2 | 1 | 1 | 0 | 0 | 0.5 |
| 3 | 0 | 1 | 0 | 1 | 0.5 |
| 5 | 0 | 0 | 0 | 0 | 0 |

The foregoing descriptions are merely preferred examples of the present disclosure and are not intended to limit the present disclosure in any form. Although the present disclosure has been disclosed by way of preferred examples, it is to be understood that the invention is not limited thereto. A person skilled in the art can make some equivalent variations or modifications to the above-disclosed technical content without departing from the scope of the technical solutions of the present disclosure to obtain equivalent examples. An example present disclosure simple modifications, equivalent changes and modifications made to the above examples according to the technical essence of the present disclosure all fall within the scope of the technical solutions of the present disclosure without departing from the contents of the technical solutions of the present disclosure.

What is claimed is:

1. A porcine pseudorabies virus gB protein fragment, wherein by using a sequence of gB protein in PVR HN1201 strain shown in SEQ ID NO: 2 as a reference site, an amino acid sequence of the gB protein fragment consists of a sequence represented by amino acids 62-148 of gB protein and a sequence represented by amino acids 546-700 of gB protein, or the gB protein fragment consists of a sequence represented by amino acids 62-150 of gB protein in PRV Bertha strain and a sequence represented by amino acids 548-702 of gB protein in PRV Bertha strain; or the gB protein fragment consists of a sequence represented by amino acids 62-154 of gB protein in PRV Kaplan strain and a sequence represented by amino acids 552-706 of gB protein in PRV Kaplan strain; or the gB protein fragment consists of a sequence represented by amino acids 62-147 of gB protein in PRV Becker strain and a sequence represented by amino acids 545-699 of gB protein in PRV Becker strain, the gB protein fragment is capable of maintaining antigenic activity of the gB protein.

2. The porcine pseudorabies virus gB protein fragment as described in claim 1, wherein the amino acid sequence of the gB protein fragment is an amino acid sequence of SEQ ID NO: 4, SEQ ID NO: 6, SEQ ID NO: 8, or SEQ ID NO: 10.

3. A porcine pseudorabies virus gB-gD protein, wherein the gB-gD protein comprises the gB protein fragment as described in claim 1, and gD protein, which are tandem-expressed or fusion-expressed.

4. The porcine pseudorabies virus gB-gD protein as described in claim 3, wherein an amino acid sequence of the gD protein fragment is an amino acid sequence of SEQ ID NO: 12.

5. A subunit vaccine of porcine pseudorabies virus, wherein the subunit vaccine comprises an immune amount of the gB-gD protein as described in claim 3 and an adjuvant.

6. The subunit vaccine of porcine pseudorabies virus as described in claim 5, wherein content of the gB-gD protein fragment is 25-100 μg/ml.

7. The subunit vaccine of porcine pseudorabies virus as described in claim 5, wherein an amino acid sequence of the gD protein fragment is an amino acid sequence of SEQ ID NO: 12.

8. A subunit vaccine of porcine pseudorabies virus, wherein the subunit vaccine comprises an immune amount of a porcine pseudorabies virus gB protein fragment, and an adjuvant, wherein by using a sequence of gB protein in PVR HN1201 strain shown in SEQ ID NO: 2 as a reference site, an amino acid sequence of the gB protein fragment consists of a sequence represented by amino acids 62-148 of gB protein and/or a sequence represented by amino acids 546-700 of gB protein, or the gB protein fragment consists of a sequence represented by amino acids 62-150 of gB protein in PRV Bertha strain and a sequence represented by amino acids 548-702 of gB protein in PRV Bertha strain; or the gB protein fragment consists of a sequence represented by amino acids 62-154 of gB protein in PRV Kaplan strain and a sequence represented by amino acids 552-706 of gB protein in PRV Kaplan strain; or the gB protein fragment consists of a sequence represented by amino acids 62-147 of gB protein in PRV Becker strain and a sequence represented by amino acids 545-699 of gB protein in PRV Becker strain, the gB protein fragment is capable of maintaining antigenic activity of the gB protein.

9. The subunit vaccine of porcine pseudorabies virus as described in claim 8, wherein content of the gB protein fragment is 25-100 μg/ml.

10. The subunit vaccine of porcine pseudorabies virus as described in claim 8, wherein the gB protein fragment consists of a sequence represented by amino acids 62-148 of gB protein in PRV HN1201 strain and a sequence represented by amino acids 546-700 of gB protein in PRV HN1201 strain, or the gB protein fragment consists of a sequence represented by amino acids 62-150 of gB protein in PRV Bertha strain and a sequence represented by amino acids 548-702 of gB protein in PRV Bertha strain; or the gB protein fragment consists of a sequence represented by amino acids 62-154 of gB protein in PRV Kaplan strain and a sequence represented by amino acids 552-706 of gB protein in PRV Kaplan strain; or the gB protein fragment consists of a sequence represented by amino acids 62-147 of gB protein in PRV Becker strain and a sequence represented by amino acids 545-699 of gB protein in PRV Becker strain.

11. The subunit vaccine of porcine pseudorabies virus as described in claim 10, wherein the amino acid sequence of the gB protein fragment is an amino acid sequence of SEQ ID NO: 4, SEQ ID NO: 6, SEQ ID NO: 8, or SEQ ID NO: 10.

12. A preparation method of a subunit vaccine, wherein the method comprises:

1) a step of cloning a nucleotide sequence of the gB protein fragment as described in claim 1;
2) a step of expressing the cloned nucleotide sequence of the step 1) to obtain the gB protein fragment; and
3) a step of preparing a subunit vaccine by adding an adjuvant to the gB protein fragment obtained from the step 2).

13. A preparation method of a subunit vaccine, wherein the method comprises:

1) a step of cloning a nucleotide sequence of the gB protein fragment as described in claim 1, and cloning a nucleotide sequence of the gD protein;
2) a step of tandem-expressing or fusion-expressing the cloned nucleotide sequence of the step 1) to obtain the gB-gD protein; and
3) a step of preparing subunit vaccine by adding an adjuvant to the gB-gD protein obtained from step 2).

* * * * *